United States Patent
Gillespie et al.

(10) Patent No.: US 10,092,690 B2
(45) Date of Patent: Oct. 9, 2018

(54) INFUSION PUMP INCLUDING SYRINGE SENSING

(71) Applicant: BAXTER INTERNATIONAL INC., Deerfield, IL (US)

(72) Inventors: John Gillespie, Naperville, IL (US); Ralph H. LaBedz, McHenry, IL (US); Michael Kenneth Platt, Mt. Prospect, IL (US); Ronald H. Spang, Kenosha, WI (US); James Frei Berrill, Cary, IL (US); Matthew Stephen Vogel, Round Lake, IL (US); Michelle Kowalski Greaney, Grayslake, IL (US)

(73) Assignee: Baxter International Inc., Deerfield, IL (US)

( * ) Notice: Subject to any disclaimer, the term of this patent is extended or adjusted under 35 U.S.C. 154(b) by 0 days.

(21) Appl. No.: 15/363,593

(22) Filed: Nov. 29, 2016

(65) Prior Publication Data

US 2017/0072133 A1 Mar. 16, 2017

Related U.S. Application Data

(60) Division of application No. 14/215,958, filed on Mar. 17, 2014, now Pat. No. 9,514,518, which is a
(Continued)

(51) Int. Cl.
*A61M 5/142* (2006.01)
*A61M 5/172* (2006.01)
(Continued)

(52) U.S. Cl.
CPC ........ *A61M 5/142* (2013.01); *A61M 5/14566* (2013.01); *A61M 5/172* (2013.01);
(Continued)

(58) Field of Classification Search
CPC ............ A61M 5/14566; A61M 5/1456; A61M 5/14546; A61M 5/142; A61M 5/172;
(Continued)

(56) References Cited

U.S. PATENT DOCUMENTS

| 3,756,752 | A | 9/1973 | Stenner |
| 3,771,694 | A | 11/1973 | Kaminski |

(Continued)

FOREIGN PATENT DOCUMENTS

| EP | 0 215 249 | 3/1987 |
| EP | 0 447 985 | 9/1991 |

(Continued)

OTHER PUBLICATIONS

International Search Report for International Application No. PCT/US 02/36963 of Applicant Baxter International Inc.
(Continued)

*Primary Examiner* — Manuel Mendez
(74) *Attorney, Agent, or Firm* — K&L Gates LLP

(57) ABSTRACT

An infusion pump operable with a syringe having a syringe barrel and a syringe plunger includes a housing having a compartment to receive the syringe and defining a wall, and a syringe clamp moveable towards and away from the wall, the syringe clamp contacting the syringe barrel; a drive mechanism supported and structured and arranged to contact and end of the syringe plunger so as to be able to move the syringe plunger within the syringe barrel; a syringe barrel size sensor including a magnet operably coupled to the syringe clamp, and a sensing member supported by the housing and configured to generate an output indicative of a magnetic field associated with the magnet; and software installed on the pump and programmed to use the output to determine a size of the syringe barrel received by the compartment.

22 Claims, 16 Drawing Sheets

Related U.S. Application Data continuation of application No. 12/573,620, filed on Oct. 5, 2009, now Pat. No. 8,696,632, which is a continuation of application No. 11/319,350, filed on Dec. 28, 2005, now Pat. No. 7,608,060, which is a division of application No. 10/172,807, filed on Jun. 14, 2002, now Pat. No. 7,018,361.

(51) Int. Cl.
 G01B 7/00 (2006.01)
 G06T 3/60 (2006.01)
 A61M 5/145 (2006.01)
(52) U.S. Cl.
 CPC .............. *G01B 7/00* (2013.01); *G01B 7/003* (2013.01); *G06T 3/60* (2013.01); *A61M 5/1456* (2013.01); *A61M 2005/14208* (2013.01); *A61M 2005/14573* (2013.01); *A61M 2205/21* (2013.01); *A61M 2205/6054* (2013.01); *A61M 2205/8206* (2013.01); *A61M 2205/8237* (2013.01); *A61M 2209/086* (2013.01)
(58) Field of Classification Search
 CPC ...... A61M 16/183; A61M 2005/14208; A61M 2005/14573; A61M 2205/21; A61M 2205/6054; A61M 2205/8206; A61M 2205/8237; A61M 2209/086; G01B 7/00; G01B 7/003; G06T 3/60
 USPC ................ 604/65–67, 151, 131; 128/DIG. 1, 128/DIG. 12, DIG. 13; 417/15
 See application file for complete search history.

(56) References Cited

U.S. PATENT DOCUMENTS

| | | |
|---|---|---|
| 3,809,871 A | 5/1974 | Howard et al. |
| 3,998,103 A | 12/1976 | Bjorklund et al. |
| 4,151,407 A | 4/1979 | McBride et al. |
| 4,199,307 A | 4/1980 | Jassawalla |
| 4,237,409 A | 12/1980 | Sugalski |
| 4,273,121 A | 6/1981 | Jassawalla |
| 4,277,226 A | 7/1981 | Archibald |
| 4,308,866 A | 1/1982 | Jelliffe et al. |
| 4,320,757 A | 3/1982 | Whitney et al. |
| 4,369,780 A | 1/1983 | Sakai |
| 4,398,908 A | 8/1983 | Siposs |
| 4,424,720 A * | 1/1984 | Bucchianeri ........ A61M 5/1456 128/DIG. 1 |
| 4,428,381 A | 1/1984 | Hepp |
| 4,443,216 A | 4/1984 | Chappell |
| 4,451,255 A | 5/1984 | Bujan et al. |
| 4,460,358 A | 7/1984 | Somerville et al. |
| 4,472,116 A | 9/1984 | Wenstrup |
| 4,487,604 A | 12/1984 | Iwatschenko et al. |
| 4,493,710 A | 1/1985 | King et al. |
| 4,496,351 A | 1/1985 | Hillel et al. |
| 4,511,352 A | 4/1985 | Theeuwes et al. |
| 4,529,401 A | 7/1985 | Leslie et al. |
| 4,544,369 A | 10/1985 | Skakoon et al. |
| 4,551,133 A | 11/1985 | Zegers de Beyl et al. |
| 4,559,038 A | 12/1985 | Berg et al. |
| 4,561,830 A | 12/1985 | Bradley |
| 4,565,542 A | 1/1986 | Berg |
| 4,596,550 A | 6/1986 | Troutner |
| 4,601,702 A | 7/1986 | Hudson |
| 4,602,249 A | 7/1986 | Abbott |
| 4,624,661 A | 11/1986 | Arimond |
| 4,637,817 A | 1/1987 | Archibald et al. |
| 4,648,812 A | 3/1987 | Kobayashi et al. |
| 4,650,469 A | 3/1987 | Berg et al. |
| 4,652,260 A * | 3/1987 | Fenton, Jr. ........ A61M 5/1456 128/DIG. 12 |
| 4,652,262 A | 3/1987 | Veracchi |
| 4,676,776 A | 6/1987 | Howson |
| 4,681,563 A | 7/1987 | Deckert et al. |
| 4,690,673 A | 9/1987 | Bloomquist |
| 4,696,671 A | 9/1987 | Epstein et al. |
| 4,718,576 A | 1/1988 | Tamura et al. |
| 4,722,224 A | 2/1988 | Scheller et al. |
| 4,722,734 A | 2/1988 | Kolln |
| 4,725,205 A | 2/1988 | Cannon et al. |
| 4,731,058 A | 3/1988 | Doan |
| 4,741,732 A | 5/1988 | Crankshaw et al. |
| 4,754,401 A | 6/1988 | Kaczynski et al. |
| 4,756,706 A | 7/1988 | Kerns et al. |
| 4,810,243 A | 3/1989 | Howson |
| 4,836,752 A | 6/1989 | Burkett |
| 4,838,857 A * | 6/1989 | Strowe ............... A61M 5/1456 128/DIG. 12 |
| 4,854,324 A | 8/1989 | Hirschman et al. |
| 4,886,431 A | 12/1989 | Soderquist et al. |
| 4,908,017 A | 3/1990 | Howson et al. |
| 4,923,375 A | 5/1990 | Ejlersen |
| 4,931,041 A | 6/1990 | Faeser |
| 4,936,760 A | 6/1990 | Williams |
| 4,941,808 A | 7/1990 | Qureshi et al. |
| 4,943,279 A | 7/1990 | Samiotes et al. |
| 4,954,046 A | 9/1990 | Irvin et al. |
| 4,960,230 A | 10/1990 | Marelli |
| 5,034,004 A | 7/1991 | Crankshaw |
| 5,041,086 A | 8/1991 | Koenig et al. |
| 5,053,031 A | 10/1991 | Borsanyi |
| 5,055,001 A | 10/1991 | Natwick et al. |
| 5,057,081 A | 10/1991 | Sunderland |
| 5,061,243 A | 10/1991 | Winchell et al. |
| 5,078,362 A | 1/1992 | Lawless et al. |
| 5,078,683 A | 1/1992 | Sancoff et al. |
| 5,088,904 A | 2/1992 | Okada |
| 5,098,256 A | 3/1992 | Smith |
| 5,098,377 A | 3/1992 | Borsanyi et al. |
| 5,100,380 A | 3/1992 | Epstein et al. |
| 5,101,679 A | 4/1992 | Smith et al. |
| 5,104,374 A | 4/1992 | Bishko et al. |
| 5,116,203 A | 5/1992 | Natwick et al. |
| 5,120,096 A | 6/1992 | D'Silva |
| 5,123,275 A | 6/1992 | Daoud et al. |
| 5,131,816 A | 7/1992 | Brown et al. |
| 5,135,500 A | 8/1992 | Zdeb |
| 5,153,827 A | 10/1992 | Coutre et al. |
| 5,160,320 A | 11/1992 | Yum et al. |
| 5,165,874 A | 11/1992 | Sancoff et al. |
| 5,176,004 A | 1/1993 | Gaudet |
| 5,181,842 A | 1/1993 | Sunderland et al. |
| 5,181,910 A | 1/1993 | Scanlon |
| 5,213,483 A | 5/1993 | Flaherty et al. |
| 5,219,327 A | 6/1993 | Okada |
| 5,219,330 A | 6/1993 | Bollish et al. |
| 5,219,331 A | 6/1993 | Vanderveen |
| 5,219,428 A | 6/1993 | Stern |
| 5,232,449 A | 8/1993 | Stern et al. |
| 5,236,416 A | 8/1993 | McDaniel et al. |
| 5,238,001 A | 8/1993 | Gallant et al. |
| 5,242,408 A | 9/1993 | Jhuboo et al. |
| 5,244,463 A | 9/1993 | Cordner, Jr. et al. |
| 5,254,096 A | 10/1993 | Rondelet et al. |
| 5,256,157 A | 10/1993 | Samiotes et al. |
| 5,261,884 A | 11/1993 | Stern et al. |
| 5,265,431 A | 11/1993 | Gaudet et al. |
| 5,279,556 A | 1/1994 | Goi et al. |
| 5,290,239 A | 3/1994 | Classey et al. |
| 5,295,966 A | 3/1994 | Stern et al. |
| 5,295,967 A | 3/1994 | Rondelet et al. |
| 5,298,021 A | 3/1994 | Sherer |
| 5,317,506 A | 5/1994 | Coutre et al. |
| 5,330,431 A | 7/1994 | Herskowitz |
| 5,336,245 A | 8/1994 | Adams et al. |
| 5,338,157 A | 8/1994 | Blomquist |
| 5,341,291 A | 8/1994 | Roizen et al. |
| 5,348,539 A | 9/1994 | Herskowitz |
| 5,361,963 A | 11/1994 | Ozawa |
| 5,366,904 A | 11/1994 | Qureshi et al. |

(56) References Cited

U.S. PATENT DOCUMENTS

| | | | |
|---|---|---|---|
| 5,370,612 A | 12/1994 | Maeda et al. | |
| 5,374,251 A | 12/1994 | Smith | |
| 5,374,965 A | 12/1994 | Kanno | |
| 5,376,070 A | 12/1994 | Purvis et al. | |
| 5,378,231 A | 1/1995 | Johnson et al. | |
| 5,387,088 A | 2/1995 | Knapp et al. | |
| 5,389,078 A | 2/1995 | Zalesky et al. | |
| 5,395,320 A | 3/1995 | Padda et al. | |
| 5,397,222 A | 3/1995 | Moss et al. | |
| 5,423,746 A | 6/1995 | Burkett et al. | |
| 5,429,602 A | 7/1995 | Hauser | |
| 5,431,627 A | 7/1995 | Pastrone et al. | |
| 5,437,635 A | 8/1995 | Fields et al. | |
| 5,462,051 A | 10/1995 | Oka et al. | |
| 5,482,446 A | 1/1996 | Williamson et al. | |
| 5,485,408 A | 1/1996 | Blomquist | |
| 5,501,665 A | 3/1996 | Jhuboo et al. | |
| 5,503,538 A | 4/1996 | Wiernicki et al. | |
| 5,507,412 A | 4/1996 | Ebert et al. | |
| 5,511,951 A | 4/1996 | O'Leary | |
| 5,513,957 A | 5/1996 | O'Leary | |
| 5,522,798 A | 6/1996 | Johnson et al. | |
| 5,522,799 A | 6/1996 | Furukawa | |
| 5,531,680 A | 7/1996 | Dumas et al. | |
| 5,531,697 A | 7/1996 | Olsen et al. | |
| 5,533,981 A | 7/1996 | Mandro et al. | |
| 5,542,921 A | 8/1996 | Meyers et al. | |
| 5,545,140 A | 8/1996 | Conero et al. | |
| 5,547,470 A | 8/1996 | Johnson et al. | |
| 5,549,460 A | 8/1996 | O'Leary | |
| 5,551,850 A | 9/1996 | Williamson et al. | |
| 5,554,115 A | 9/1996 | Thomas et al. | |
| 5,562,621 A | 10/1996 | Claude et al. | |
| 5,573,502 A | 11/1996 | LeCocq et al. | |
| 5,573,506 A | 11/1996 | Vasko | |
| D376,848 S | 12/1996 | Zeilig et al. | |
| 5,588,815 A | 12/1996 | Zaleski, II | |
| 5,589,769 A | 12/1996 | Krahn | |
| 5,601,420 A | 2/1997 | Warner et al. | |
| 5,609,575 A | 3/1997 | Larson et al. | |
| 5,620,312 A | 4/1997 | Hyman et al. | |
| 5,628,619 A | 5/1997 | Wilson | |
| 5,630,710 A | 5/1997 | Tune et al. | |
| D380,260 S | 6/1997 | Hyman | |
| 5,637,093 A | 6/1997 | Hyman et al. | |
| 5,647,853 A | 7/1997 | Feldmann et al. | |
| 5,647,854 A | 7/1997 | Olsen et al. | |
| 5,662,612 A * | 9/1997 | Niehoff | A61M 5/14546 417/15 |
| 5,669,877 A | 9/1997 | Blomquist | |
| 5,681,285 A | 10/1997 | Ford et al. | |
| 5,683,367 A | 11/1997 | Jordan et al. | |
| 5,685,844 A | 11/1997 | Marttila | |
| 5,695,473 A | 12/1997 | Olsen | |
| D390,654 S | 2/1998 | Alsberg et al. | |
| 5,713,856 A | 2/1998 | Eggers et al. | |
| 5,745,378 A | 4/1998 | Barker et al. | |
| 5,752,976 A | 5/1998 | Duffin et al. | |
| 5,766,155 A | 6/1998 | Hyman et al. | |
| 5,776,345 A | 7/1998 | Truitt et al. | |
| 5,782,805 A | 7/1998 | Meinzer et al. | |
| 5,788,669 A | 8/1998 | Peterson | |
| 5,791,880 A | 8/1998 | Wilson | |
| 5,795,327 A | 8/1998 | Wilson et al. | |
| 5,807,322 A | 9/1998 | Lindsey et al. | |
| 5,807,336 A | 9/1998 | Russo et al. | |
| 5,813,972 A | 9/1998 | Nazarian et al. | |
| 5,814,015 A * | 9/1998 | Gargano | A61M 5/1456 604/151 |
| 5,842,841 A | 12/1998 | Danby et al. | |
| 5,853,386 A | 12/1998 | Davis et al. | |
| 5,868,710 A | 2/1999 | Battiato et al. | |
| 5,871,465 A | 2/1999 | Vasko | |
| 5,885,245 A | 3/1999 | Lynch et al. | |
| 5,894,273 A | 4/1999 | Meador et al. | |
| 5,895,371 A | 4/1999 | Levitas et al. | |
| 5,897,530 A | 4/1999 | Jackson | |
| 5,904,668 A | 5/1999 | Hyman et al. | |
| 5,906,589 A | 5/1999 | Gordon et al. | |
| 5,935,099 A | 8/1999 | Peterson et al. | |
| 5,935,106 A | 8/1999 | Olsen | |
| 5,943,633 A | 8/1999 | Wilson et al. | |
| 5,951,510 A | 9/1999 | Barak | |
| 5,993,420 A | 11/1999 | Hyman et al. | |
| 6,004,020 A | 12/1999 | Bartur | |
| 6,024,539 A | 2/2000 | Blomquist | |
| 6,064,797 A | 5/2000 | Crittendon et al. | |
| 6,117,115 A | 9/2000 | Hill et al. | |
| 6,135,949 A | 10/2000 | Russo et al. | |
| 6,145,695 A | 11/2000 | Garrigues | |
| 6,154,214 A | 11/2000 | Uyehara et al. | |
| 6,173,198 B1 | 1/2001 | Schulze et al. | |
| 6,203,528 B1 | 3/2001 | Deckert et al. | |
| 6,231,560 B1 | 5/2001 | Bui et al. | |
| 6,297,795 B1 | 10/2001 | Kato et al. | |
| 6,348,952 B1 | 2/2002 | Kumi | |
| 6,358,225 B1 | 3/2002 | Butterfield | |
| 6,423,035 B1 | 7/2002 | Das et al. | |
| 6,458,102 B1 | 10/2002 | Mann et al. | |
| 6,475,180 B2 | 11/2002 | Peterson et al. | |
| 6,485,465 B2 | 11/2002 | Moberg et al. | |
| 6,500,151 B1 | 12/2002 | Cobb et al. | |
| 6,584,336 B1 | 6/2003 | Ali et al. | |
| 6,585,675 B1 | 7/2003 | O'Mahony et al. | |
| 6,585,684 B1 | 7/2003 | Hughett et al. | |
| 6,592,551 B1 | 7/2003 | Cobb | |
| 6,645,177 B1 | 11/2003 | Shearn | |
| 6,952,551 B2 | 10/2005 | Koyanagi et al. | |
| 7,394,244 B2 | 7/2008 | Schley et al. | |
| 7,422,570 B2 | 9/2008 | Gerlach et al. | |
| 7,452,190 B2 | 11/2008 | Bouton et al. | |
| 7,543,516 B2 | 6/2009 | Siefert | |
| 7,635,349 B2 | 12/2009 | Tribe et al. | |
| 8,161,810 B2 | 4/2012 | Cadieux et al. | |
| 2001/0031944 A1 | 10/2001 | Peterson et al. | |
| 2001/0034502 A1 | 10/2001 | Moberg et al. | |
| 2001/0044602 A1 | 11/2001 | Angersbach et al. | |
| 2002/0004645 A1 | 1/2002 | Carlisle et al. | |
| 2002/0128606 A1 | 9/2002 | Cowan et al. | |
| 2002/0165491 A1 | 11/2002 | Reilly | |
| 2002/0188259 A1 * | 12/2002 | Hickle | A61M 16/183 604/189 |
| 2003/0009133 A1 | 1/2003 | Ramey | |
| 2003/0060754 A1 | 3/2003 | Reilly et al. | |
| 2003/0060768 A1 | 3/2003 | Kiyatake et al. | |
| 2003/0065287 A1 | 4/2003 | Spohn et al. | |
| 2003/0073954 A1 | 4/2003 | Moberg et al. | |
| 2003/0078534 A1 | 4/2003 | Hochman et al. | |
| 2003/0097092 A1 | 5/2003 | Flaherty | |
| 2003/0149402 A1 | 8/2003 | Gerlach et al. | |

FOREIGN PATENT DOCUMENTS

| | | |
|---|---|---|
| EP | 0 522 527 | 1/1993 |
| EP | 0 560 270 | 9/1993 |
| EP | 0 567 944 | 11/1993 |
| EP | 0 567 945 | 11/1993 |
| EP | 0 567 946 | 11/1993 |
| EP | 0 567 962 | 11/1993 |
| EP | 1 679 091 | 7/2006 |
| GB | 2 190 145 | 11/1987 |
| GB | 2 208 897 | 4/1989 |
| GB | 2 336 510 | 10/1999 |
| JP | 2001-178821 | 7/2001 |
| WO | WO 84/04685 | 12/1984 |
| WO | WO 92/03656 | 3/1992 |
| WO | WO 93/05829 | 4/1993 |
| WO | WO 95/17913 | 7/1995 |
| WO | WO 00/42911 | 7/2000 |

(56) References Cited

FOREIGN PATENT DOCUMENTS

| WO | WO 00/48112 | 8/2000 |
| WO | WO 00/68766 | 11/2000 |

OTHER PUBLICATIONS

International Search Report for International Application No. PCT/US 02/36964 of Applicant Baxter International Inc.
Canadian Office Action received Feb. 13, 2013 for related Canadian Appln. No. 2,756,560.
Canadian Office Action, Appl. No. 2,854,094, dated Apr. 15, 2015—3 pages.
Final Office Action for U.S. Appl. No. 10/172,804 dated Aug. 25, 2005.
Final Office Action for U.S. Appl. No. 90/009,778 dated Feb. 16, 2011.
Non-Final Office Action for U.S. Appl. No. 10/172,804 dated Mar. 7, 2005.
Non-Final Office Action for U.S. Appl. No. 90/009,778 dated Nov. 19, 2010.
Request for Ex Parte Reexamination Under 35 U.S.C. 302 and 37 C.F.R. 1.510 for U.S. Appl. No. 10/172,804 filed Jul. 8, 2010.
Response After Final Office Action for U.S. Appl. No. 10/172,804 dated Sep. 20, 2005.
Response to Office Action for U.S. Appl. No. 10/172,804 dated Jun. 7, 2005.
IPRP—PCT/US02/36962—dated Jul. 15, 2010—6 pages.

\* cited by examiner

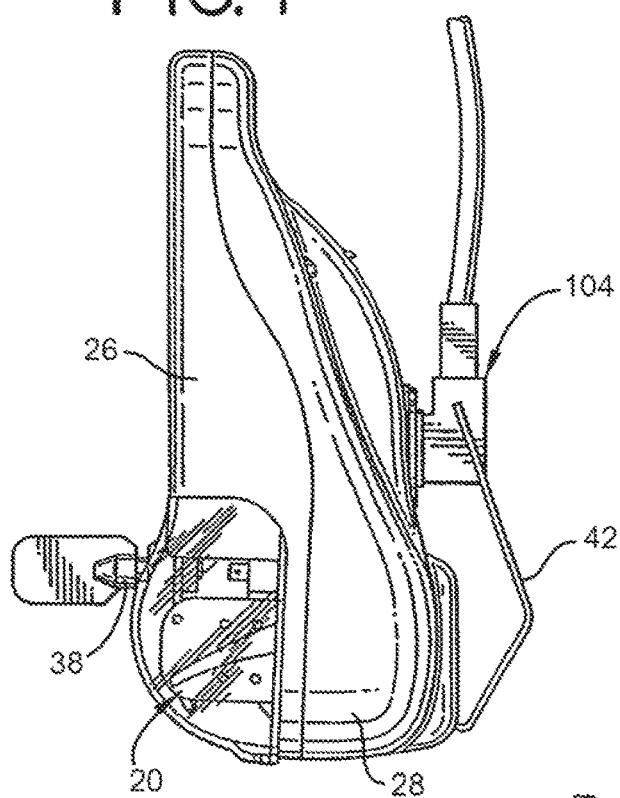
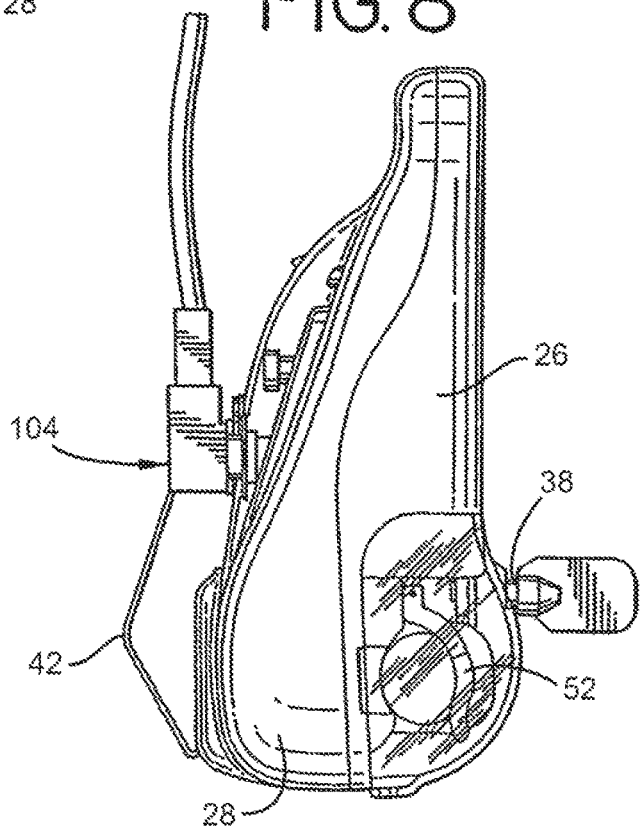

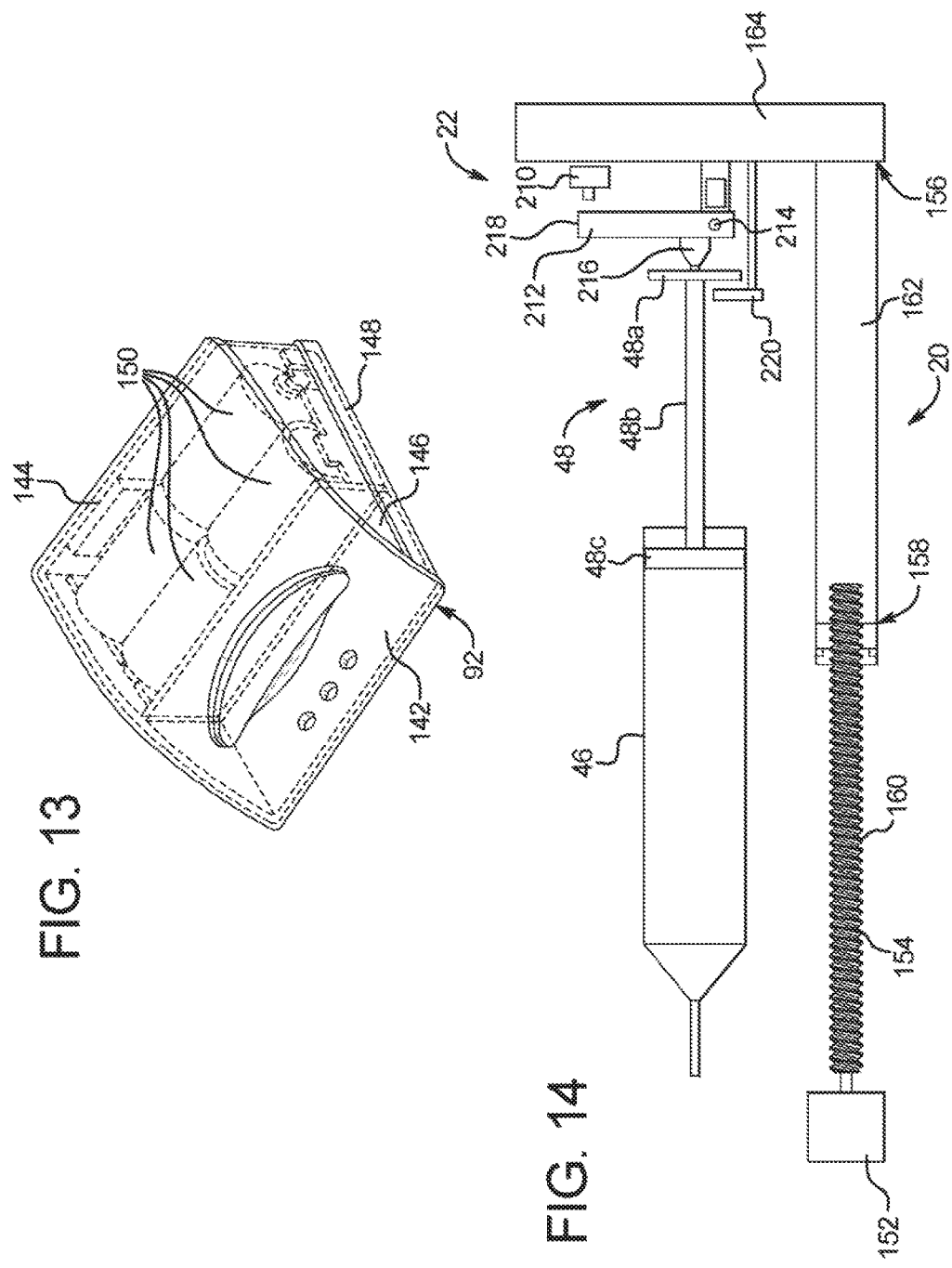

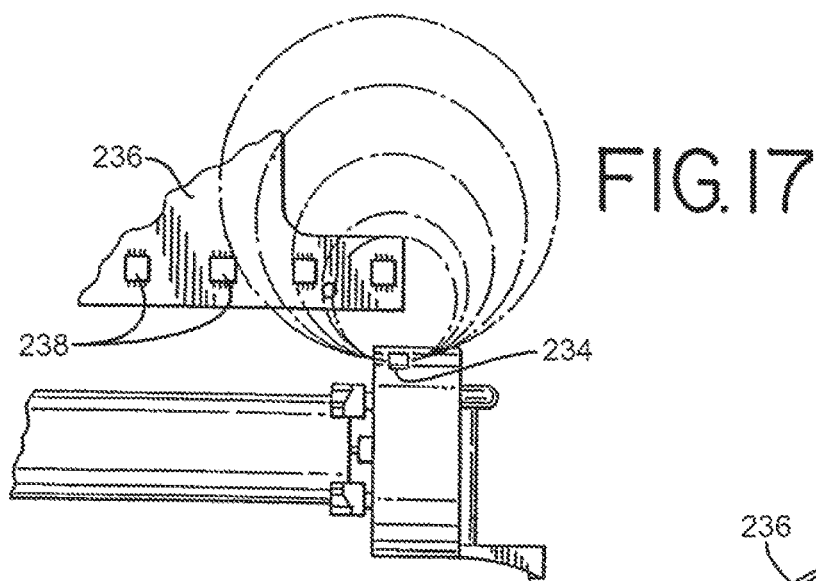
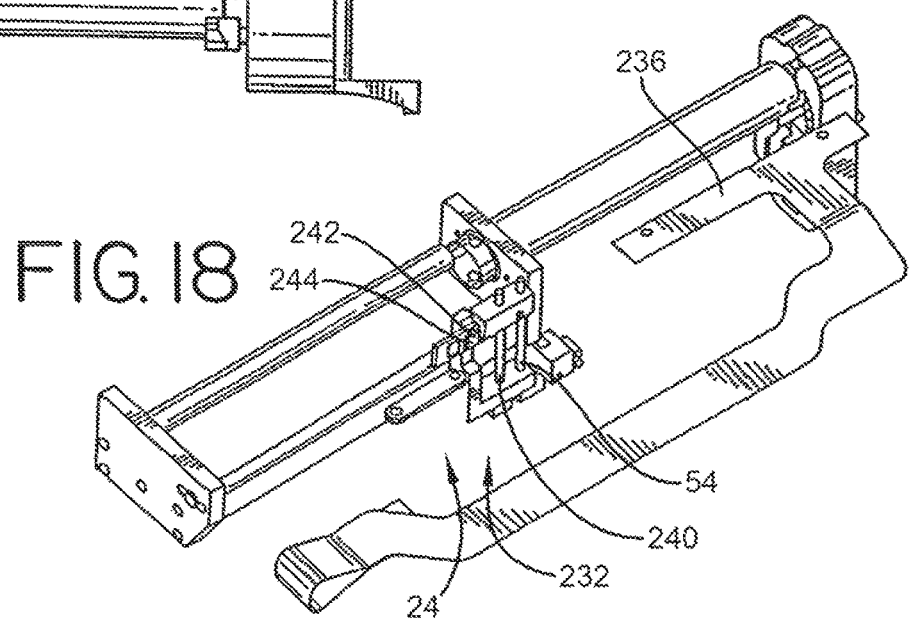
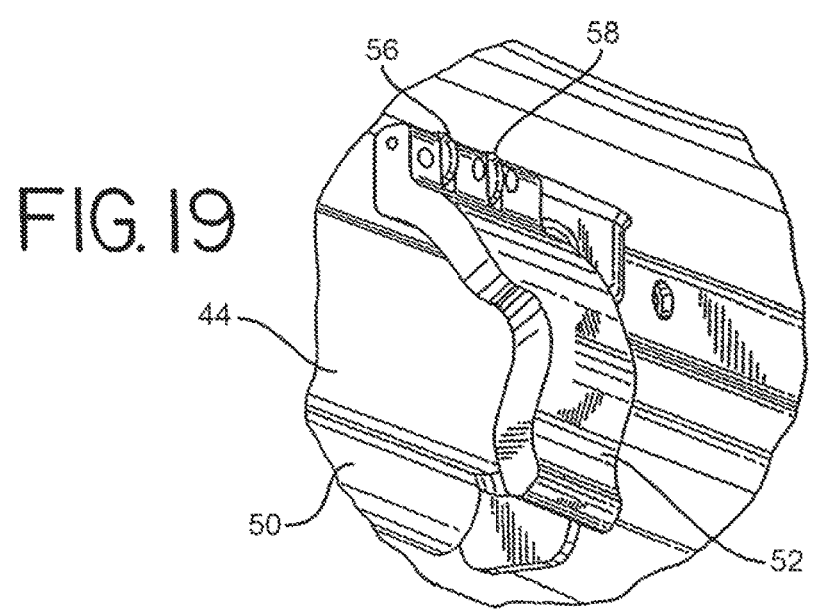

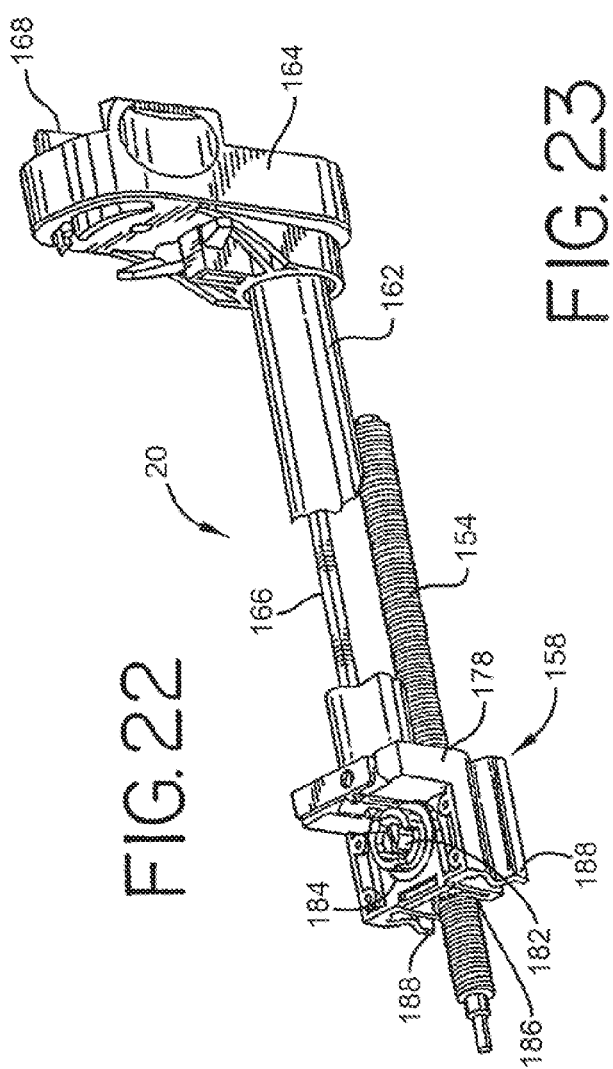
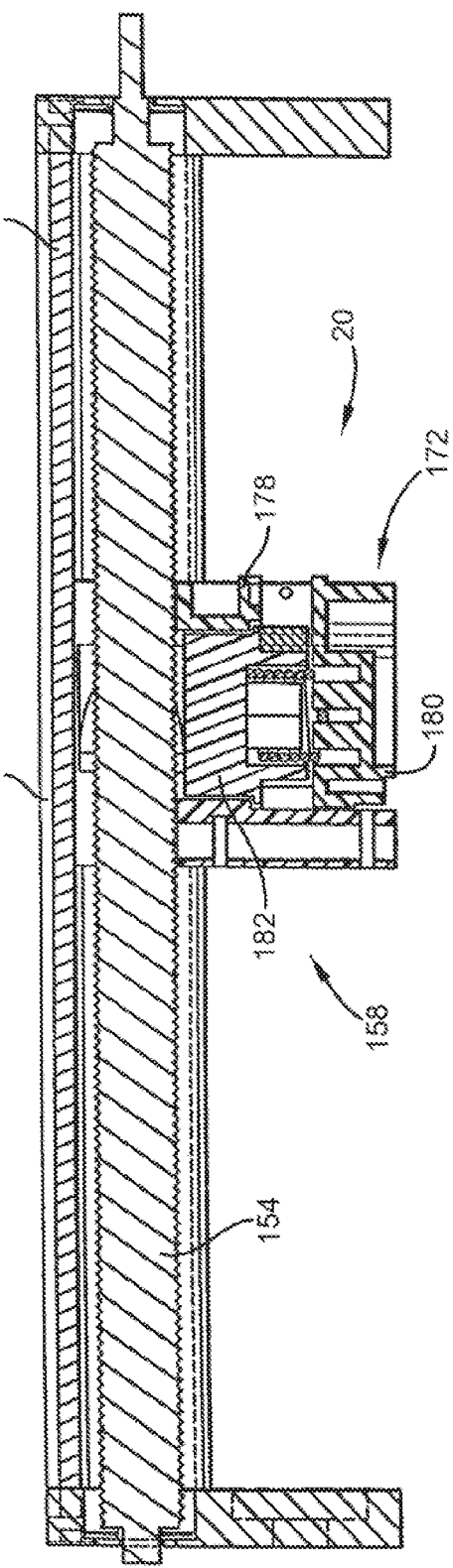

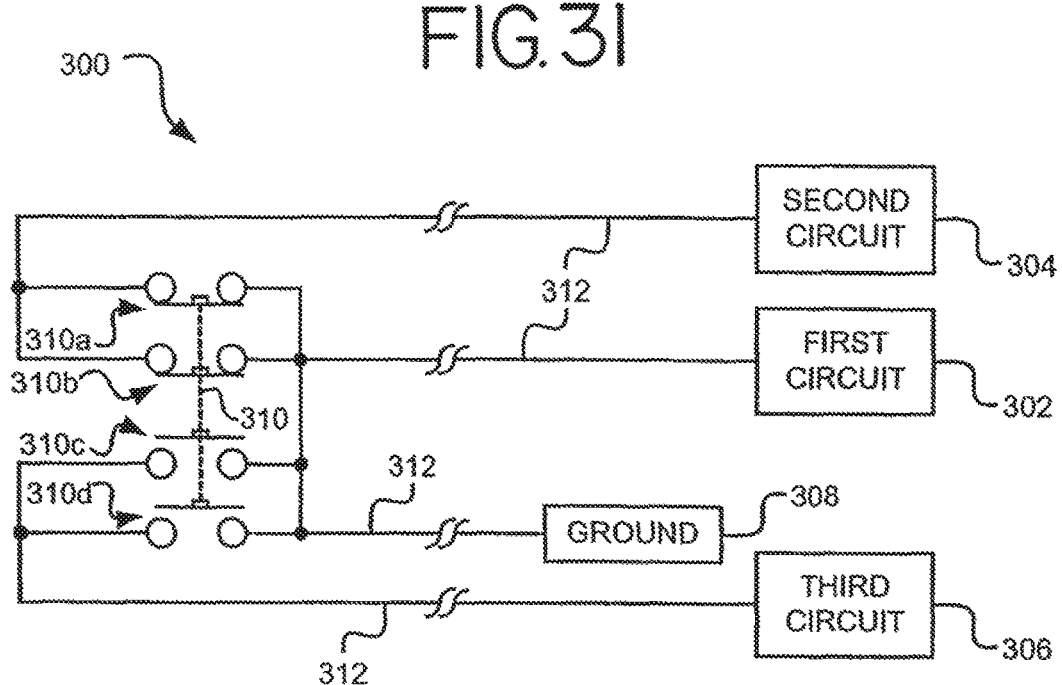
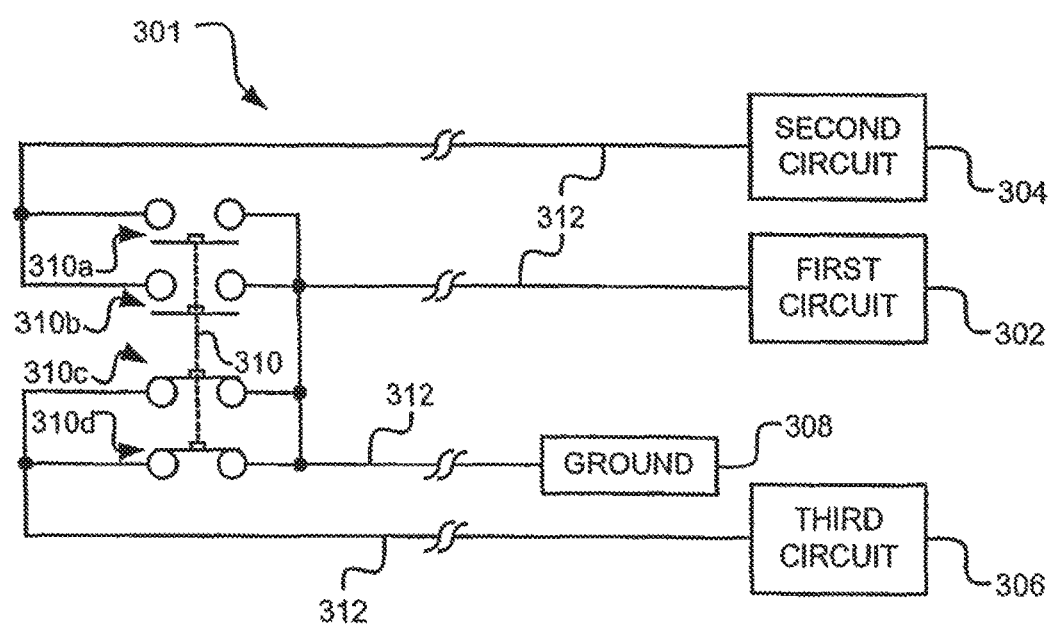

FIG. 33

| CONDITION | FIRST CIRCUIT | SECOND CIRCUIT | THIRD CIRCUIT |
|---|---|---|---|
| PCA NOT INSTALLED | HIGH | HIGH | HIGH |
| PCA FAULT | HIGH | LOW | HIGH |
| PCA FAULT | HIGH | HIGH | LOW |
| PCA FAULT | HIGH | LOW | LOW |
| PCA FAULT | LOW | HIGH | HIGH |
| PCA INSTALLED | LOW | LOW | HIGH |
| BOLUS ACTUATED | LOW | HIGH | LOW |
| PCA FAULT | LOW | LOW | LOW |

INFUSION PUMP INCLUDING SYRINGE SENSING

PRIORITY CLAIM

This application claims priority to and the benefit as a divisional application of U.S. patent application Ser. No. 14/215,958, entitled "Infusion Pump Including Syringe Plunger Position Sensor", filed Mar. 17, 2014, issued as U.S. Pat. No. 9,514,518, which is a continuation application of U.S. patent application Ser. No. 12/573,620, entitled "Infusion Pump With Battery Operation Capability", filed Oct. 5, 2009, issued as U.S. Pat. No. 8,696,632, which is continuation application of U.S. patent application Ser. No. 11/319,350, entitled "Infusion Pump", filed Dec. 28, 2005, issued as U.S. Pat. No. 7,608,060, which is a divisional application of U.S. patent application Ser. No. 10/172,807, entitled "Infusion Pump", filed Jun. 14, 2002, issued as U.S. Pat. No. 7,018,361, the entire contents of each of which are incorporated herein by reference and relied upon.

BACKGROUND

The present invention relates to a pump and more particularly to an infusion pump for the delivery of a medication to a patient.

Generally, medical patients sometimes require precise delivery of either continuous medication or medication at set periodic intervals. Medical pumps have been developed to provide controlled drug infusion wherein the drug can be administered at a precise rate that keeps the drug concentration within a therapeutic margin and out of an unnecessary or possibly toxic range. Basically, the medical pumps provide appropriate drug delivery to the patient at a controllable rate which does not require frequent attention.

Medical pumps may facilitate administration of intravenous therapy to patients both in and outside of a clinical setting. Outside a clinical setting, doctors have found that in many instances patients can return to substantially normal lives, provided that they receive periodic or continuous intravenous administration of medication. Among the types of therapies requiring this kind of administration are antibiotic therapy, chemotherapy, pain control therapy, nutritional therapy, and several other types known by those skilled in the art. In many cases, patients receive multiple daily therapies. Certain medical conditions require infusions of drugs in solution over relatively short periods such as from 30 minutes to two hours. These conditions and others have combined to promote the development of increasingly lightweight, portable or ambulatory infusion pumps that can be worn by a patient and are capable of administering a continuous supply of medication at a desired rate, or provide several doses of medication at scheduled intervals.

Configurations of infusion pumps include elastomeric pumps, which squeeze solution from flexible containers, such as balloons, into IV tubing for delivery to the patient. Alternatively, spring-loaded pumps pressurize the solution containers or reservoirs. Certain pump designs utilize cartridges containing flexible compartments that are squeezed by pressure rollers for discharging the solutions, such as in U.S. Pat. No. 4,741,736. Other references which disclose portable infusion pumps include U.S. Pat. No. 5,330,431 (showing an infusion pump in which standard pre-filled single dosage IV bags are squeezed by the use of a roller); U.S. Pat. No. 5,348,539 (showing an infusion pump in which prepackaged IV bags are squeezed by a bladder which is actuated by fluid pumped from a reservoir); U.S. Pat. No. 5,429,602 (showing a programmable portable infusion pump system for injecting one or more medicinal substances into an individual); and U.S. Pat. No. 5,554,123 (showing an infusion pump in which the amount of fluid required to pump a bladder sufficient to fully dispense solution from a bag is less than the volume of an IV bag.). Infusion pumps utilizing syringes are also known wherein a drive mechanism moves a plunger of the syringe to deliver fluid to a patient. Typically, these infusion pumps include a housing adapted to receive a syringe assembly, a drive mechanism adapted to move the syringe plunger, a pump control unit having a variety of operating controls, and a power source for powering the pump including the drive mechanism and controls.

While the discussed prior art and other designs have recognized the need for an infusion pump which is smaller and more compact for mobile use by ambulatory patients or other patients, each has failed to address the need for a more suitable power source. Naturally, a portable pump must be supplied with an equally portable power source as a means for powering the pump motor. Batteries are a suitable choice of power for portable units. Some prior art pumps may use disposable batteries while other pumps may use rechargeable batteries.

Disposable batteries have proven to have a longer life than the life of a rechargeable battery (with a single charge). Disposable batteries are also typically smaller than rechargeable battery units. However, there is an environmental disposal concern with such batteries, as they place a considerable burden on the environment. Disposable batteries are responsible for a major share of heavy metal pollution in domestic waste. Despite special collection efforts and consumer awareness campaigns, a high percentage of batteries sold still end up in domestic waste sites. Heavy metals eventually leak from the batteries into the ground soil, damaging the environment.

Environmental concerns are greatly alleviated if rechargeable batteries are used in place of disposable batteries. However, where such batteries or battery packs are rechargeable, an AC outlet is usually necessary. A separate charger, as is well-known in the art, is also required for the recharging effort. Unfortunately, these facilities are not always readily available or accessible to the patient and, with respect to the usual adapters and extension cords, they add to the bulk and weight of the infusion pump system. Furthermore, in certain pumps utilizing rechargeable batteries, the pump itself must be used in the recharging effort as it typically houses the transformer used in the recharging process.

Batteries and battery packs that are large and bulky significantly add to the weight of the portable infusion pump. Weight and size of the infusion pump is an important consideration because it may be carried about by nurses or other hospital personnel. The pump must also be sized to be attached to an I.V. pole. The I.V. pole, with attached pump, may be moved about in a hospital setting. In addition, where interrupted operation of the pump may have negative consequences, extra batteries or an extra battery pack may be added to the carrying necessities of the infusion pump. In some instances, the carrying of a second set of batteries or a back-up battery pack may double the weight of the power source.

Thus, there is seen in the prior art advantages and disadvantages to both disposable and rechargeable battery powered pumps. It should be understood that under certain circumstances, a pump that uses disposable batteries may be preferable or the only option available (if no outlet is available). Under other circumstances, the benefits of lower cost and environmental concerns may dictate that rechargeable batteries are preferred.

In addition to the above, customs and/or regulations of different sovereigns may dictate the use of one type of power source for a pump over another. For example, in the U.S., pumps powered by disposable batteries have long been preferred due to their convenience and ability to provide power for extended periods of time. On the other hand, in Europe, rechargeable battery powered pumps are preferred, due to environmental concerns with the disposal of battery waste.

In light of the advantages and disadvantages that both disposable and rechargeable batteries provide, it may be desirable for some to alternate use of both battery types. However, it can be easily recognized that it would prove burdensome and a waste of space and resources to supply or have on hand two separate pumps, each utilizing a different battery type.

It may also be desirable for manufacturers of pumps to satisfy the needs of users of rechargeable battery powered pumps as well as disposable battery powered pumps. However, it is costly for manufacturers of pumps to manage entirely separate lines of pump types or forego supplying one pump type over another. Thus, it is recognized that several advantages exist for a pump that can utilize both disposable and rechargeable batteries. There exists a need in the art for a pump that may utilize both disposable and rechargeable batteries. There also remains a need for a pump that utilizes rechargeable batteries that can be re-charged without the use of the pump.

Additional problems have also been experienced with infusion pumps. For example, certain sensing systems that detect whether an occlusion is present in an infusion line have proven to be unreliable or too complex in construction. Certain syringe plunger position detectors and syringe barrel size detectors have also proven to be unreliable. In addition, drive mechanisms for syringe plungers have also proven to be unreliable as certain components become stripped or jammed adversely affecting the mechanism.

The present invention is provided to solve these and other problems.

SUMMARY

The present invention is generally directed to an infusion pump for delivering a flowable material, such as a fluid medication, to a patient through an infusion line.

According to one aspect of the invention, the infusion pump is configured to be powered by either a disposable battery or a rechargeable battery. The infusion pump has a housing having a recess. A motor is positioned within the housing and is operably connected to an electrical contact disposed in the recess. The motor powers the pump. The recess is adapted to receive one of a disposable battery unit and a rechargeable battery unit.

According to another aspect of the invention, the rechargeable battery may be in the form of a rechargeable battery unit. The rechargeable battery unit has a transformer positioned within the unit. A conductive element for providing power from an AC power outlet is coupled to the transformer. A switch is provided for receiving a first electronic signal indicative of whether the conductive element is providing power to the AC power source. A DC power source signal is provided by said AC power outlet and rectifying circuitry. A rechargeable battery source signal is provided from a receptacle within said rechargeable battery unit. The switch connects the DC power source signal to output terminals of the rechargeable battery unit only if the first electrical signal indicates that the conductive element is not providing power from the AC power source.

According to another aspect of the invention, the infusion pump is adapted to receive a syringe having a syringe barrel moveably receiving a syringe plunger therein. The infusion pump has a housing defining a compartment adapted to receive the syringe. The compartment has a rear wall. The housing further has a curved lip generally adjacent to the rear wall. A clamp is connected to the housing and is positioned in the compartment in confronting relation to the rear wall. The syringe can be loaded into the compartment between the rear wall and the clamp wherein upon initial insertion, the curved lip is adapted to slidingly engage the syringe barrel allowing generally one-hand loading of the syringe into the compartment. Syringes of a variety of different sizes can be loaded into the pump in this fashion. The curved lip has a length generally in correspondence with a length of the syringe barrel adapted to be received in the compartment. The clamp is slidable by rollers positioned at one end of the clamp.

According to another aspect of the invention, the infusion pump has a housing having a compartment adapted to receive a syringe having a barrel and a plunger. A drive mechanism is supported by the housing and is adapted to contact the plunger to move the plunger within the barrel. The drive mechanism further has a linearly moveable arm having a load cell mounted thereon. A load beam is pivotally connected to the arm. The load beam has one side contacting the load cell and another side adapted to contact the plunger. Upon movement of the arm to move the plunger, the load cell senses a reactive force from the load beam. The load cell converts the force into a usable signal wherein an occlusion is signaled if the usable signal is outside a predetermined acceptable range.

According to another aspect of the invention, the infusion pump has a syringe plunger position sensor and a syringe barrel size sensor. Each sensor utilizes a magnet/linear sensor array assembly.

According to a further aspect of the invention, the drive mechanism has a lead screw rotatably connected to a motor. A slide assembly has a threaded member wherein the threaded member is associated with the lead screw. The arm has one end connected to the slide assembly and one end adapted to be engaged with the syringe plunger. The threaded member is rotatably biased in engagement with the lead screw, wherein upon rotation of the lead screw by the motor, the slide assembly linearly moves the arm wherein the arm is adapted to move the syringe plunger within the syringe barrel. In one preferred embodiment, the threaded member is a rotary nut.

According to another aspect of the invention, the infusion pump has improved communication capabilities. The pump has a user interface having a memory for storing infusion data. The pump has a data port wherein infusion data can be transferred via infrared communication from the pump to a personal digital assistant.

Other features and advantages of the invention will be apparent from the following specification taken in conjunction with the following drawings.

BRIEF DESCRIPTION OF THE FIGURES

To understand the present invention, it will now be described by way of example, with reference to the accompanying drawings in which:

FIG. 7 is a side elevation view of the infusion pump of the present invention;

FIG. 8 is an opposite side elevation view of the infusion pump of the present invention;

FIG. 13 is a perspective view of the disposable battery unit shown in FIG. 4B;

FIG. 14 is a schematic view of a syringe drive mechanism and occlusion sensor for the infusion pump of the present invention;

FIG. 17 is a partial plan view of the syringe plunger position indicator;

FIG. 18 is a perspective underside view of the syringe drive mechanism and further showing a syringe barrel size indicator;

FIG. 19 is an enlarged partial perspective view of a syringe barrel clamp of the infusion pump of the present invention;

FIG. 22 is a partial perspective view of the syringe drive mechanism;

FIG. 23 is a partial cross-sectional view of the syringe drive mechanism;

FIG. 31 is a schematic wiring diagram of a patient controlled analgesia button associated with the pump of the present invention, the button being in an at rest position;

FIG. 32 is another schematic wiring diagram of the patient controlled analgesia button associated with the pump of the present invention, the button being in an actuated position;

FIG. 33 is a table summarizing information revealed by the circuits associated with the button of FIGS. 31 and 32

DETAILED DESCRIPTION

Figure 1:
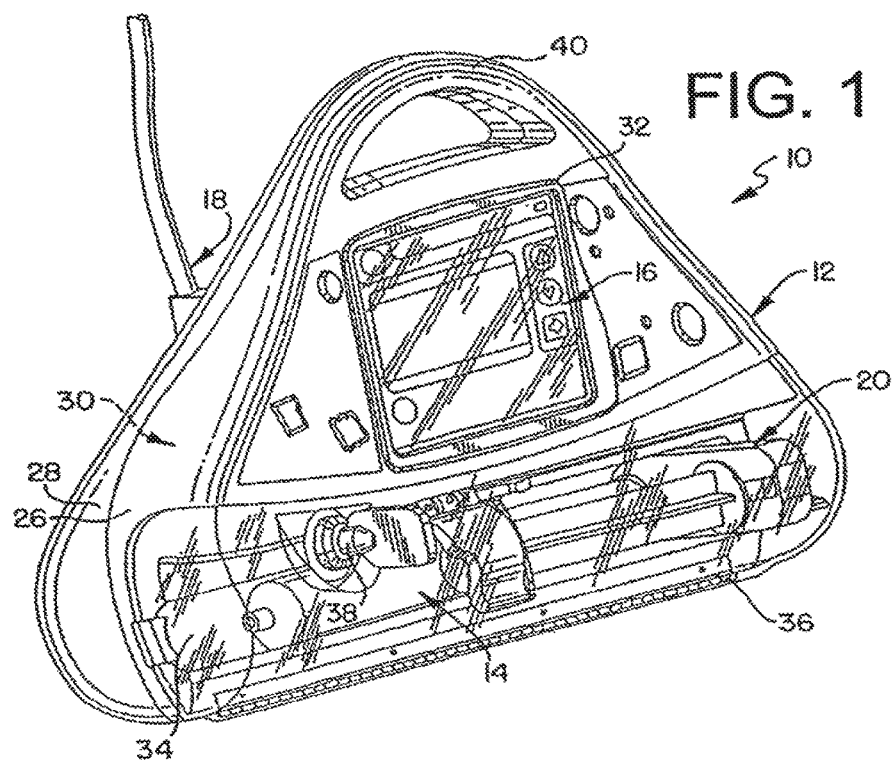
FIG. 1 is a front perspective view of one embodiment of an infusion pump which may be configured in accord with and embody the present invention.

While the present invention is susceptible of embodiment in many different forms, there is shown in the drawings and will herein be described in detail preferred embodiments of the invention with the understanding that the present disclosure is to be considered as an exemplification of the principles of the invention and is not intended to limit the broad aspect of the invention to the embodiments illustrated.

Referring to FIG. 1, therein is shown one embodiment of an infusion pump of the present invention generally referred to with the reference numeral 10. The infusion pump 10 generally includes a housing 12 that supports a syringe assembly 14, a user interface 16, a power supply 18, a drive mechanism 20 having an occlusion sensor 22 (FIG. 14), and a syringe sensor system 24 (FIGS. 15-18).

While the present invention discloses a portable infusion pump, such as, for example, a syringe-based infusion pump, and their progeny, designed and manufactured by Baxter International, Inc. of Deerfield, Ill., it is understood that individual aspects of the invention that can be incorporated into other types of pumps or other electrical or medical devices.

Figure 2:
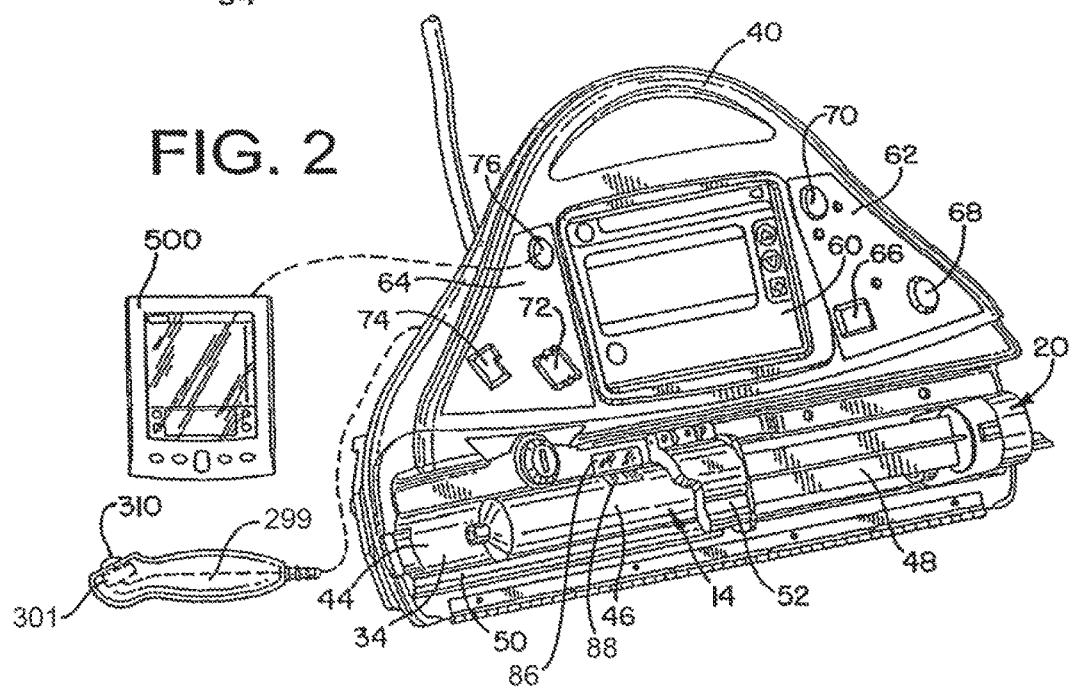
FIG. 2 is another front perspective view of the infusion pump of the present invention with an access door removed.
Figure 4A:
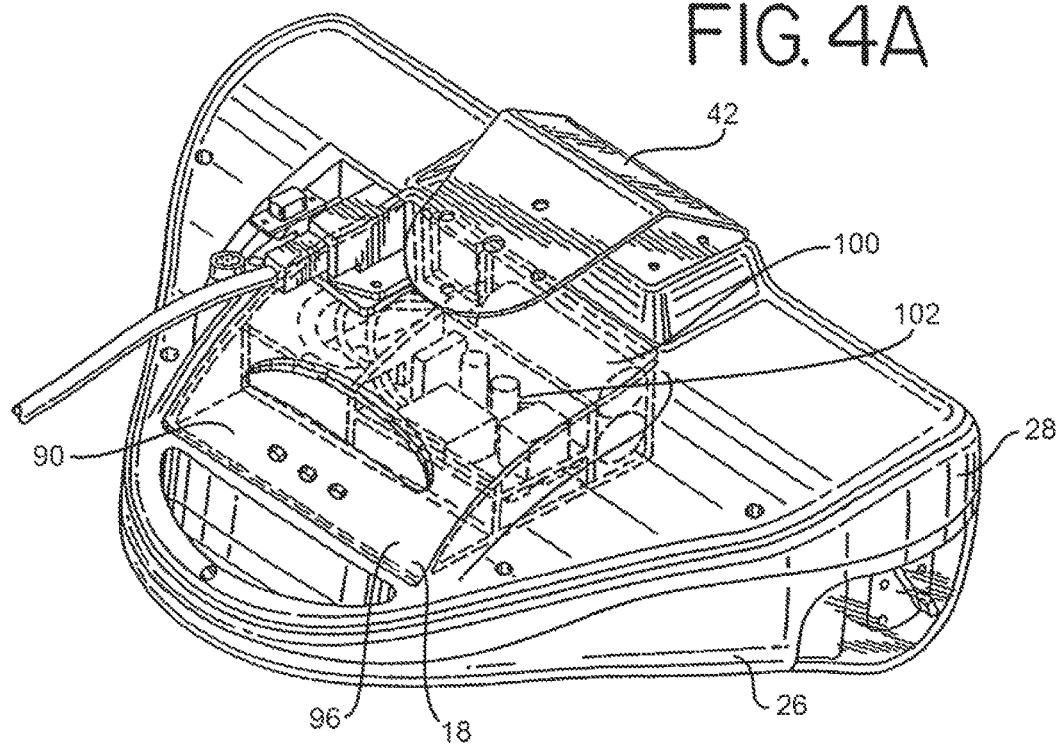
FIG. 4A is a rear perspective view of the infusion pump of the present invention, showing a rechargeable battery unit associated therewith.
Figure 4B:
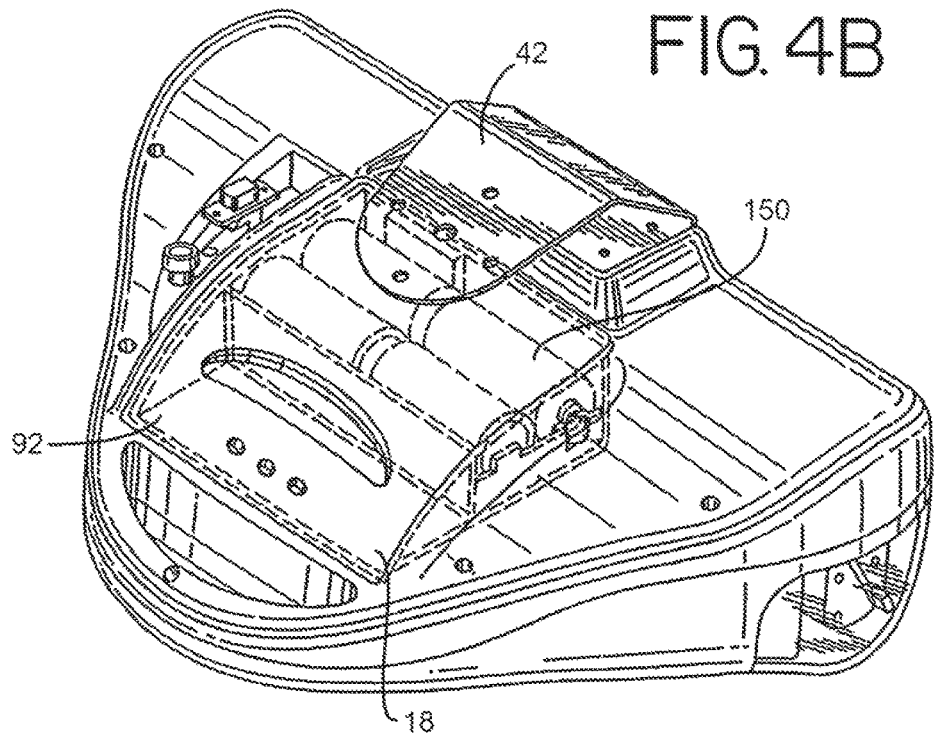
FIG. 4B is a rear perspective view of the infusion pump of the present invention, showing a disposable battery unit associated therewith.
Figure 5:
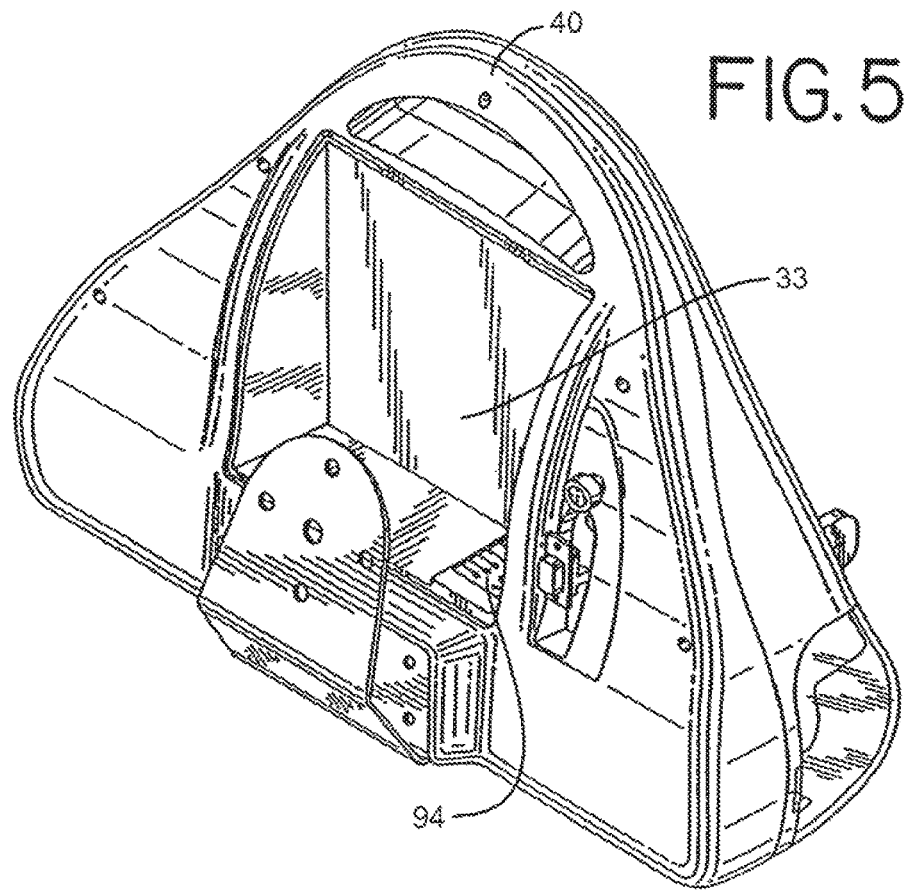
FIG. 5 is another rear perspective view of the infusion pump of the present invention with the battery unit removed.
Figure 6:
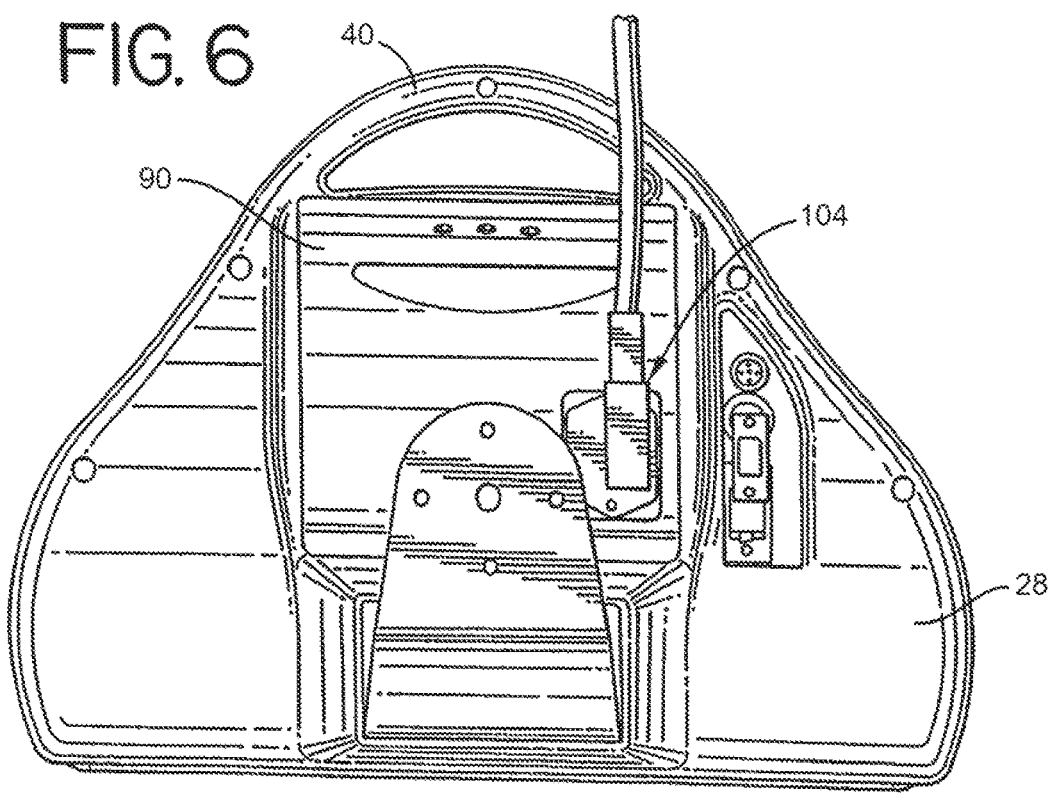
FIG. 6 is a rear elevation view of the infusion pump of the present invention.

As shown in FIGS. 1 and 2, the housing 12 of the pump 10 has a generally contoured shape. The housing 12 includes a first member 26 and a second member 28 that are connected together to form a central cavity 30. The central cavity 30 houses various components of the pump 10 including the user interface 16. The first member 26 of the housing has an opening 32 that accommodates a display screen of the user interface 16. As shown in FIG. 5, a rear portion of the housing 12 has a receptacle or recess 33 that is adapted to receive the power supply 18 to be described in greater detail below. At a bottom, front portion of the housing 12, a container compartment or syringe compartment 34 is defined that accommodates the syringe assembly 14, a portion of the drive mechanism 20 and other components. The first member 26 of the housing 12 has a hinged access door 36 that encloses the syringe assembly 14 in the compartment 34. The access door 36 is preferably transparent in order for medical personnel to view the contents in the syringe assembly 14. A lock 38 is provided with the door 36 to prevent unauthorized access to the syringe assembly 14. The lock 38 is required because oftentimes drugs such as morphine are infused by the pump 10 and can be unfortunately subject to theft. An upper portion of the housing 12 is provided with a handle 40. The housing 12 can be made from a variety of materials including various types of plastics and metals. As shown in FIG. 4-8, the housing 12 has a pole clamp 42 attached to the second member 28 of the housing 12. The pole clamp 42 can have various designs and is adapted to mount the pump 10 on a pole assembly such as used in a hospital setting. In a preferred embodiment, the pole clamp 42 is adapted to be able to mount the pump 10 in various positions. For example, the pump 10 can be mounted in a generally horizontal position shown in FIG. 3a or a generally vertical position shown in FIG. 3b.

FIG. 2 discloses the syringe compartment 34 in greater detail. Generally, the syringe compartment 34 is dimensioned to receive and support the syringe assembly 14 as well as receive a portion of a pump actuator such as the drive mechanism 20. Briefly, the syringe assembly 14 generally includes a syringe barrel 46 and a medical fluid member such as a syringe plunger 48. The syringe barrel 46 contains medication and slidably receives the syringe plunger 48. The syringe plunger 48 is driven by the drive mechanism to force medication from the syringe barrel 46 through a tube (not shown) and to a patient. The tube would have one end connected to an end of the syringe barrel 46 and another end adapted to be connected to a patient.

The syringe compartment 34 has a rear wall 44 that is generally concave to receive the syringe barrel 46 of the syringe assembly 14. The syringe barrel 46 of the syringe assembly 14 and rear wall 44 are generally in confronting relation. The housing 12 further has a curved lip 50 that in a preferred embodiment is integral with the rear wall 44. The lip 50 aids in loading a syringe assembly 14 in the compartment 34 to be described in greater detail below. As shown in FIGS. 2 and 19, a syringe clamp 52 is movably mounted in the compartment 34. The clamp 52 has a concave inner surface that faces the rear wall 44 and that fits over the syringe barrel 46. As shown in FIG. 18, the clamp 52 is slidable along a rod assembly 54 to move the clamp 52 towards and away from the rear wall 44. The clamp 52 can slide along the rod assembly 54 to accommodate different sized syringe barrels. As shown in FIG. 19, a base portion of the clamp 52 has a pair of rollers 56,58 that help reduce friction when the clamp 52 slides along the housing 12. Due to tolerances, the clamp 52 may also pivot slightly. The clamp 52 is resiliently biased towards the rear wall 44. The housing 12 and syringe compartment 34 are sized such that an entire syringe assembly, with plunger fully extended from the syringe barrel, is contained within the housing and can be enclosed by the access door 36. No part of a syringe barrel or syringe plunger protrudes from the housing 12. A portion of the drive mechanism 20 extends into the syringe compartment 34 to engage the plunger 48. The access door 36 has an opening to accommodate the tube (not shown) that is attached to the syringe barrel 46 to deliver medication to the patient.

Figure 3A:
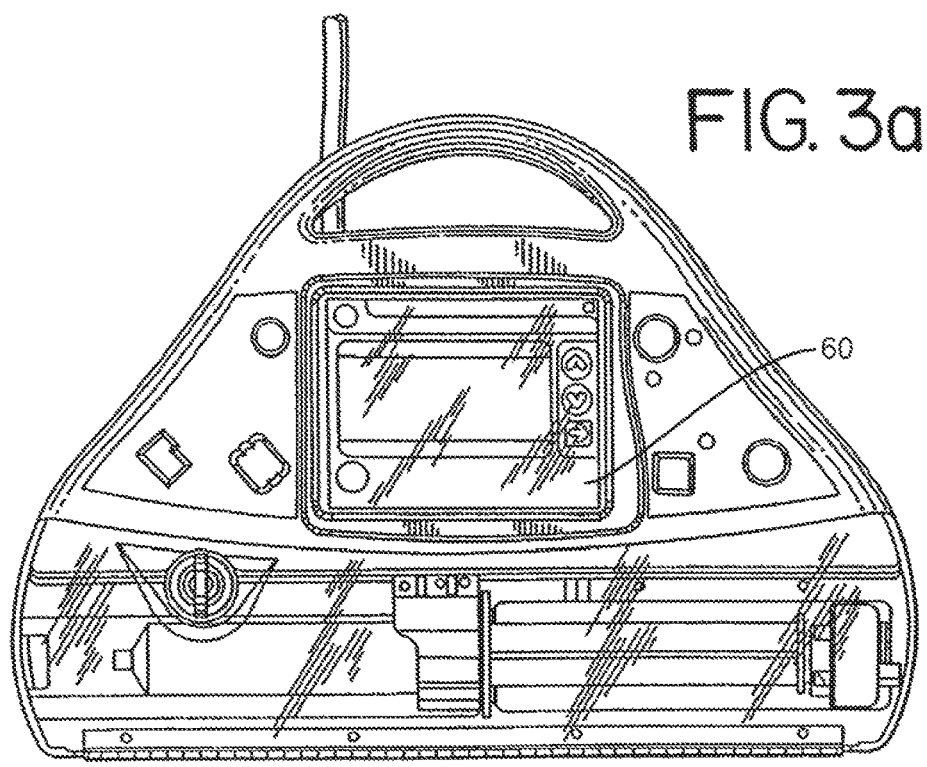
FIG. 3a is a front elevation view of the infusion pump of the present invention.
Figure 3B:
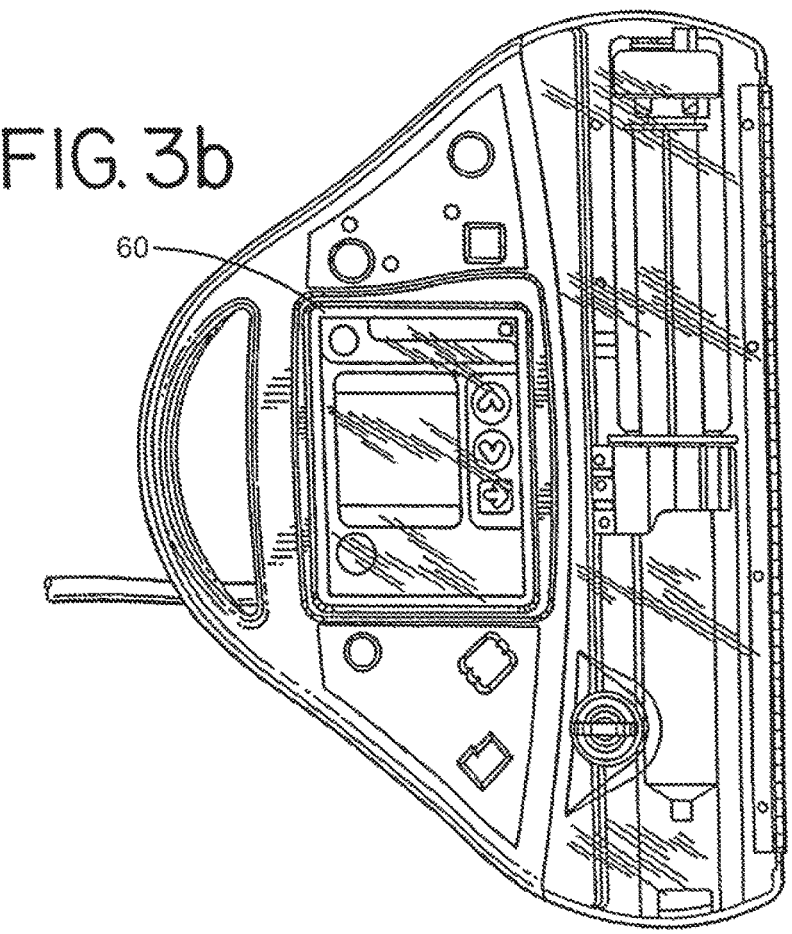
FIG. 3b is another front elevation view of the infusion pump of the present invention mounted in an alternative configuration.

As shown in FIGS. 1-3, the pump has a user interface 16. Portions of the user interface 16 are described in greater detail in commonly-owned U.S. patent application Ser. No. 10/172,808 entitled "System And Method For Operating An Infusion Pump," publication number 20040225252, now abandoned, filed concurrently herewith and incorporated by reference herein. The user interface 16 generally includes a display screen 60, a first control panel 62 and a second control panel 64, and associated electrical components and computer software contained within the housing 12 to operate the pump 10. The display screen 60 displays all of the general operating parameters of the pump 10 and fits within the opening 32 in the housing 12. The display screen 60 also acts as a touch screen for data to be inputted into the pump 10 by a user. As discussed, the pump 10 can be mounted in either a generally horizontal position (FIG. 3a) or a generally vertical position (FIG. 3b). The software associated with the user interface 16 has the ability to display information on the screen 60 in either a landscape orientation or a portrait orientation. When the pump is mounted in the horizontal configuration as shown in FIG. 3a, information is displayed on the display screen 60 in a landscape configuration. Conversely, when the pump 10 is mounted in the vertical configuration as shown in FIG. 3b, information is displayed on the display screen 60 in a portrait configuration. Thus, depending on how the pump 10 is mounted, the information can be read by users without the need to tilt one's head. This feature is described in greater detail in commonly-owned U.S. patent application Ser. No. 10/172,804 entitled "Dual-Orientation Display For Medical Devices," filed concurrently herewith, and incorporated by reference herein. The first control panel 62 generally has a start button 66, a stop button 68 and an alarm/alert button 70. The second control panel 64 generally has a settings panel 72, a history button 74 and a data port 76. These controls will be described in greater detail below.

The pump 10 and user interface 16 may utilize additional identification features regarding the medication delivered by the pump 10. For example, and as shown in FIG. 2, the pump 10 may be equipped with an RFID (radio frequency identification) reader 86 that cooperates with an RFID tag 88 attached to the syringe barrel 46. The RFID tag 86 has a transponder circuit and an antenna circuit. The RFID tag 86 can store significant information including, but not limited to, the type of medication, amount, concentration, as well as pumping parameters and instructions for the medication. The RFID reader 86 has energizer, demodulator and decoder circuits. The energizer circuit emits a low-frequency radio wave field that is used to power up the RFID tag 88. This allows the tag 88 to send its stored information to the reader 86. The information is demodulated and decoded where it then can be used by the computer associated with the user interface 16. While several different configurations are possible, the RFID reader 86 can be mounted in pump housing adjacent the syringe compartment 34. The RFID tag 88 is affixed generally to the syringe barrel 46. When the syringe assembly 14 is properly inserted into the pump 10, the RFID reader 86 automatically reads the information from the RFID tag 88, which can be used to aid in properly operating the pump 10 for a particular patient. It is understood that other types of data reader/data carrier systems can also be used.

Figure 20:
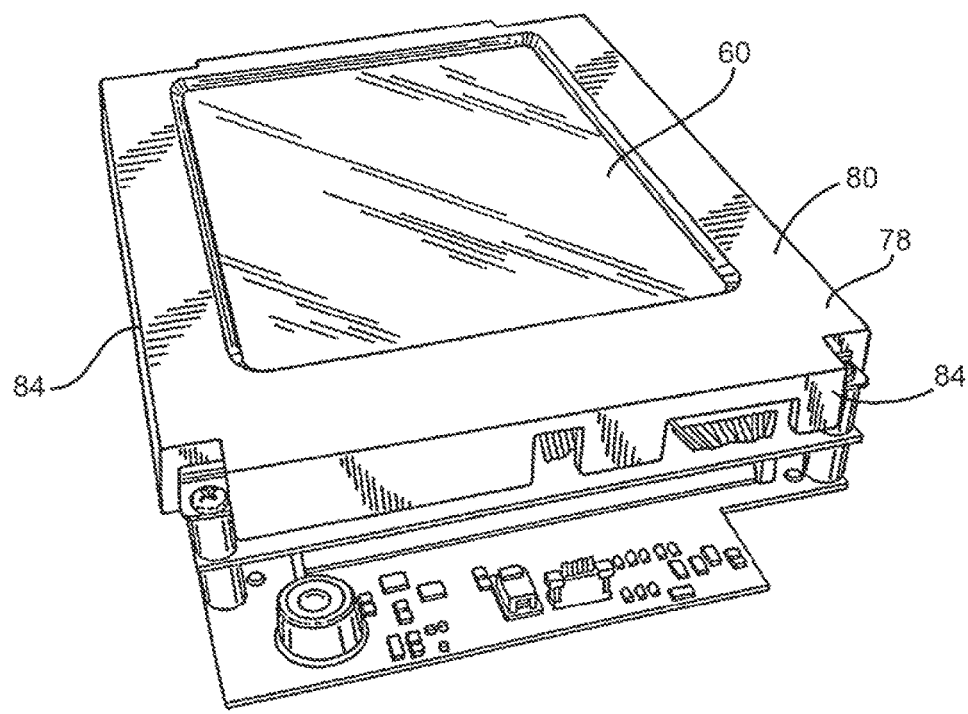
FIG. 20 is partial perspective view of a video display and pad associated with a user interface of the infusion pump of the present invention.
Figure 21:
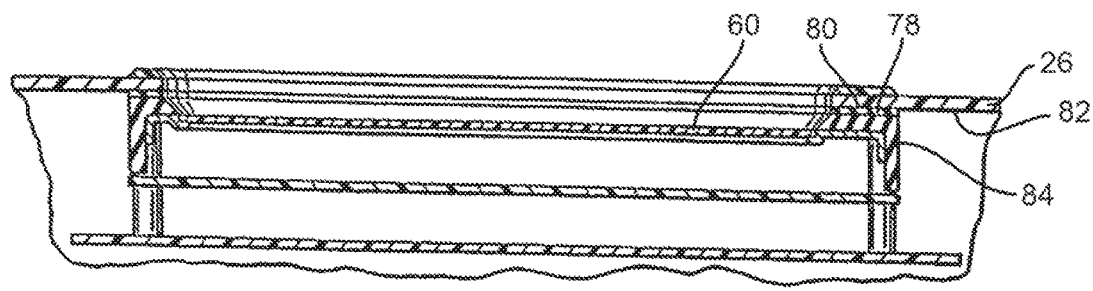
FIG. 21 is a partial cross-sectional view of the video display mounted in a housing of the infusion pump.

As shown in FIGS. 20 and 21, the display screen 60 is equipped with a pad 78 about the outer periphery of the screen 60. The pad 78 is a shock absorbent member made preferably of an elastomeric material. In one preferred embodiment, the pad 78 is made from polyurethane. The pad 78 has a face 80 that is positioned between the display screen 60 and an inner surface 82 of the first member 26 of the housing 12. The pad 78 also has a sidewall 84 preferably integral with the face 80. The pad 78 absorbs forces generated if the pump 10 is jostled, bumped or dropped, and minimizes the effect such occurrences have on the display screen 60. The pad 78 also resists fluid infiltration into the housing 12.

The pump 10 of the present invention includes the power supply 18 that can take many different forms. In one preferred embodiment, the power supply 18 may be in the form of a rechargeable battery unit 90 or a disposable battery unit 92. The rechargeable battery unit 90 is generally shown in FIG. 4a and the disposable battery unit 92 is generally shown in FIG. 4b. The pump 10 will operate with either unit 90,92 depending on the needs and desires of the user. As shown in FIG. 5, the pump 10 has an electrical contact 94 positioned in the recess 33 that is in electrical communication with the user interface components of the pump 10 as is known. The contact 94 will cooperate with a corresponding electrical contact on either of the rechargeable battery unit 90 or the disposable battery unit 92 as will be described.

Figure 9:
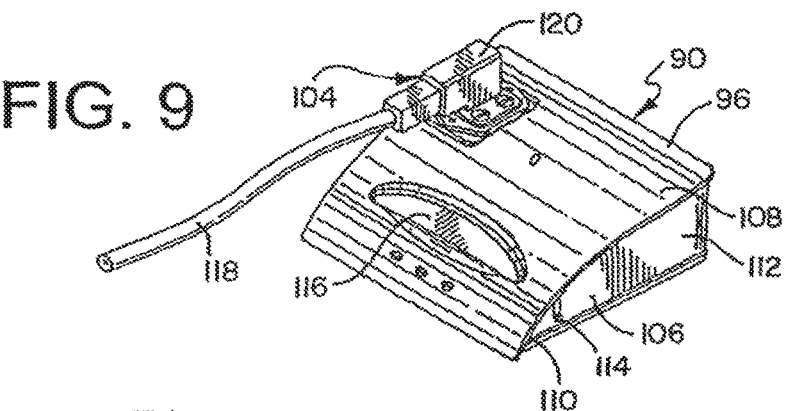
FIG. 9 is a perspective view of the rechargeable battery unit shown in FIG. 4A.
Figure 10:
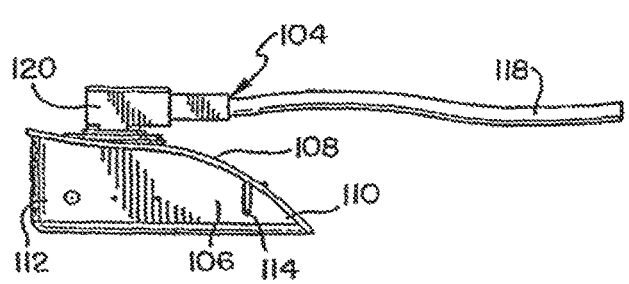
FIG. 10 is a side elevation view of the rechargeable battery unit shown in FIG. 9.
Figure 11:
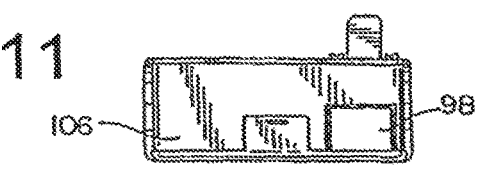
FIG. 11 is an end elevation view of the rechargeable battery unit shown in FIG. 9.

FIGS. 4a and 6-12 generally disclose the rechargeable battery unit 90. FIGS. 9-11 show the rechargeable battery unit 90 removed from the pump 10. As shown in FIGS. 4a and 11, the rechargeable battery unit 90 generally includes a battery housing 96 having an electrical contact 98 to cooperate with the pump housing electrical contact 94, a rechargeable battery 100, associated electrical components 102, and an AC power supply assembly 104.

As shown in FIGS. 9-11, the rechargeable battery unit housing 96 generally has a base member 106 and a cover member 108. The base member 106 and cover member 108 are contoured wherein the housing 96 has a shallow first end 110 and a deeper second end 112. The contour of the housing 96 is generally similar to the outer contour of the backside of the pump housing 12. FIG. 4a, 6-8 show the unit 90 installed in the pump housing 12 illustrating the corresponding contours. As shown in FIG. 11, a bottom portion of the base member 106 supports the electrical contact 98, and contacts the housing electrical contact 94 when the unit 90 is installed. As further shown, the battery unit housing 96 has a pair of posts 114 that laterally protrude from the housing 96. The posts 114 cooperate with retainers in the pump housing 12 to retain the unit 90 within the housing 12. A push button 116 is included on the housing cover 108 to retract the posts 114 when removing the unit 90 from the pump housing 12.

As further shown in FIGS. 9 and 10, the AC power supply assembly 104 has a power cord 118 and an associated terminal 120 that plugs into the housing 96. The AC power supply assembly 104 has a plug that can be inserted into a standard electrical outlet to recharge the rechargeable battery 100 when necessary. AC power can also be supplied through the assembly 104 to power the pump 10.

Figure 12:
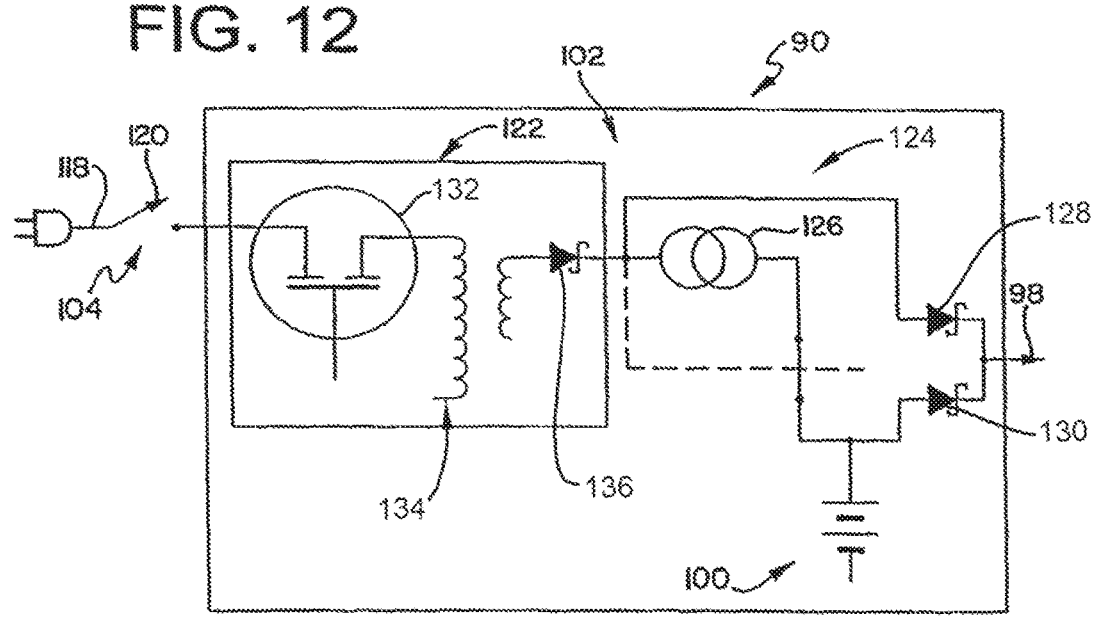
FIG. 12 is a electrical schematic view of the rechargeable battery unit.

FIG. 12 schematically shows the electrical components 102 that are associated with the rechargeable battery unit 90. The electrical components 102 generally include a power supply 122 and a recharger assembly 124 that includes a recharger 126 and a diode mechanism in the form of a first diode 128 and a second diode 130. The power supply 122, in one preferred embodiment, is an off-line switching power supply. The power supply 122 generally includes a field-effect transistor (FET) 132, connected to a transformer 134, which in turn is connected to a power supply diode 136. The power supply 122 has one connection to the AC power supply assembly 104. The power supply 122 is also connected to the recharger 126. The diodes 128,130 are generally connected to the recharger 126, the power supply 122, the rechargeable battery 100 and the terminal 98 so as to provide the desired power through the unit 90. For example, when the plug of the AC power supply assembly 104 is not plugged into a wall outlet as shown in FIG. 12, the first and second diodes 128,130 are biased and configured such that power is being supplied by the rechargeable battery 100. If the plug of the assembly 104 is plugged into a wall outlet, the power supply 122 provides 12 volts. When the 12 volts are sensed, the diodes 128, 130 are configured such that the rechargeable battery 100 is being recharged by the power supply 122 and the unit 90 is supplying power through the power supply 122 via the plugged in AC power supply assembly 104. Accordingly, power can be switched from being supplied from the rechargeable battery 100 or from the wall outlet. It is further noted that because the rechargeable battery unit 90 houses the power supply 122, the recharger 126 and the rechargeable battery 100 within the unit 90, the battery 100 can be recharged without the use of the pump 10.

The battery 100 can be charged simply by plugging the cord of the power assembly 104, connected to the unit 90, into a wall outlet. The unit 90 need not be installed into the pump 10. In prior art pumps, the pump itself is needed to recharge the battery. It is also understood that the rechargeable battery unit 90 can be defined without the AC power cord assembly 104 wherein the assembly 104 is considered a separate component removably attachable to the unit 90. The battery units 90,92 may also be equipped with a microchip that is capable of transmitting data to the user interface 16 of the pump 10 such as the amount of charge left in the batteries being utilized.

FIGS. 4b and 13 generally disclose the disposable battery unit 92. The general structure of the disposable battery unit 92 is similar to the rechargeable battery unit 90. The disposable battery unit has a housing 142 having an electrical contact 144 that will cooperate with the housing electrical contact 94 in the housing recess 33 (See FIGS. 4b and 5). The housing 142 has a base member 146 and a cover member 148. The base member 146 receives a plurality of disposable batteries 150, and in a preferred embodiment, four D-cell batteries are utilized. It is understood, however, that other battery configurations are possible. The batteries are supported such that the batteries will supply electrical power through the contact 144 as is known. As shown in FIG. 4b, the disposable battery unit 92 is received by the recess 33 of the pump 10 in the same fashion as the rechargeable battery unit 90 shown in FIG. 4a.

Thus, depending on the desires of the user, the pump 10 may be powered by the rechargeable battery unit 90 or the disposable battery unit 92. The pump 10 may be provided with multiple units 90,92 wherein the pump 10 can remain in use by replacing the unit 90,92 requiring either recharging, or new disposable batteries.

FIGS. 14, 15 and 22-30 disclose the syringe drive mechanism 20. FIG. 14 represents a simplified schematic view. The syringe drive mechanism 20 is accommodated by the pump housing 12 and generally includes a motor 152, a lead screw 154, a connecting linkage 156 and a slide assembly 158. Briefly, the connecting linkage 156 is connected to the slide assembly 158, which is associated with the lead screw 154. The slide assembly 158 which moves linearly in response to rotation of the lead screw 154 by the motor 152. Linear movement of the connecting linkage 156 moves the syringe plunger 48, having a plunger flange 48a, a plunger arm 48b and plunger stopper 48c, within the syringe barrel 46 to expel fluid from the syringe assembly 14.

As shown in FIG. 14, the motor 152 is operably connected to the lead screw 154 to rotate the lead screw 154 when the motor 152 is energized. The lead screw 154 has threads 160 that cooperate with a threaded member of the slide assembly 158 as will be described in greater detail below.

FIGS. 14-18 and 22 generally show the connecting linkage 156. The connecting linkage 156 generally includes a tube member 162 and a plunger engagement arm 164. The tube member 162 is connected at one end to the slide assembly 158 and at another end to the plunger engagement arm 164. As shown in FIG. 22, the tube member 162 houses a rod 166 that is connected to a lever 168 pivotally mounted on the engagement member 164. As explained in greater detail below, the rod 166, when actuated by the lever 168, can disengage the slide assembly 158 from the lead screw 154. This allows the slide assembly 158 to freely slide along the lead screw 154 to linearly position the plunger engagement arm 164 against the plunger 48 extending from the syringe barrel 46.

As further shown in FIGS. 14, 15 and 22-23, the slide assembly 158 generally includes a rail member 170 and a slide member 172. The rail member 170 has a pair of legs 174 depending from a cover plate 176. The slide member 172 slides beneath the cover plate 176 as can be appreciated from FIG. 15. The legs 174 have an inwardly protruding portion 175. The rail member 170 is positioned within the housing 12 and adjacent the rear wall 44 of the syringe compartment 34.

As shown in FIGS. 22-27, the slide member 172 generally has a base 178 and a cover 180 that collectively support a threaded member 182 or rotary nut 182 therein. The base 178 has a countersunk bore 184 therethrough that is in communication with a channel 186. The bore receives the rotary nut 182 and the channel 186 accommodates a portion of the rotary nut 182 and the lead screw 154. The base 178 has a pair of cantilevered beams 188 that correspond in shape to the legs 174 of the rail member 170. The beams 188 are slightly biased into frictional sliding engagement with the legs 174 and provide a smooth sliding movement of the slide member 172 along the rail member 170. As shown in FIG. 23, the cover 180 fits over the rotary nut 182. The cover 180 supports additional structure such as a pin 185 and lock arm 187 (See FIG. 24). This structure will be described in greater detail below.

Figure 28:
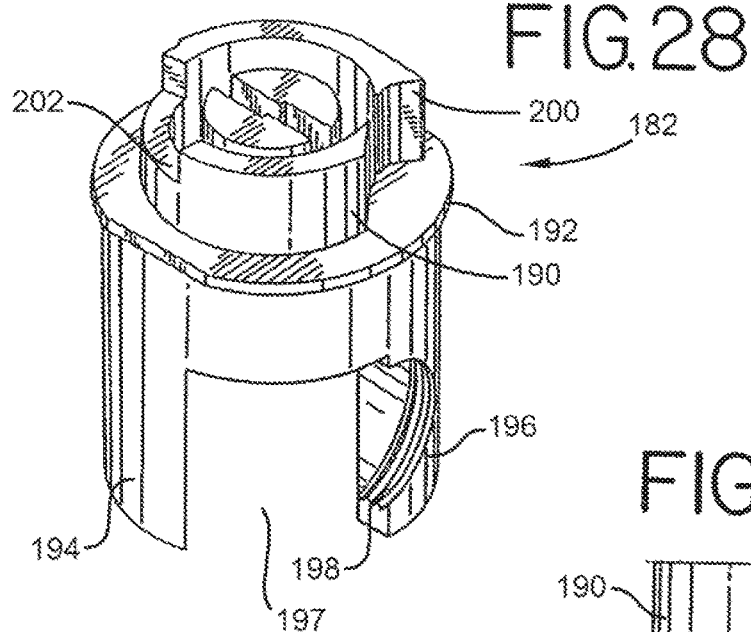
FIG. 28 is a perspective view of the rotary nut.
Figure 29:
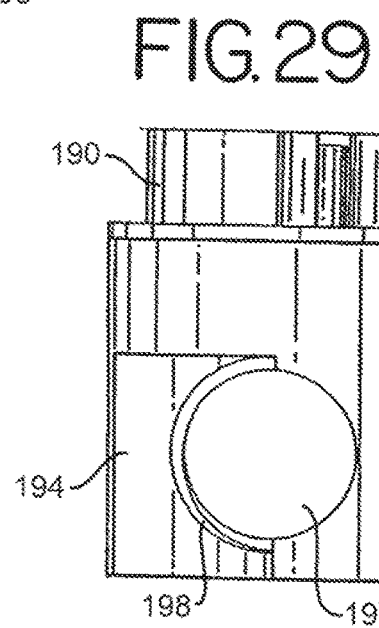
FIG. 29 is an elevation view of the rotary nut.
Figure 30:
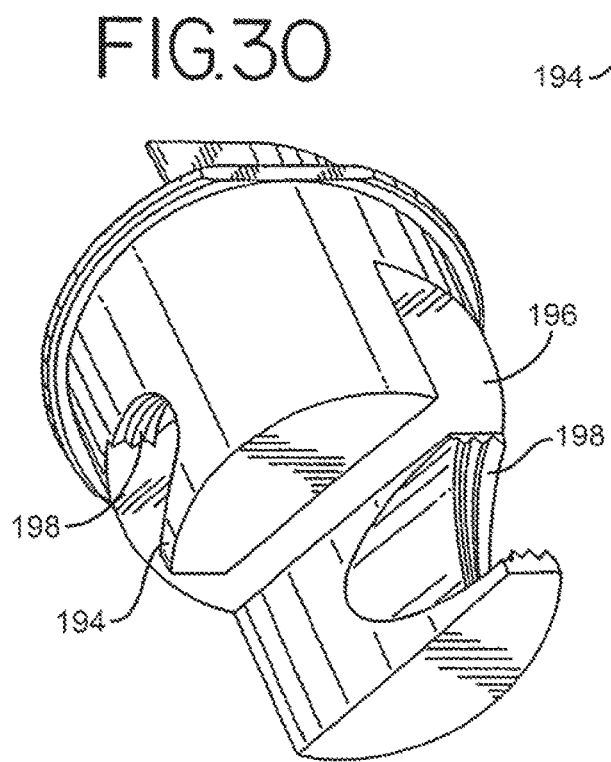
FIG. 30 is an underside perspective view of the rotary nut.

FIGS. 28-30 further disclose the rotary nut 182. The rotary nut 182 is a unitary member having a generally cylindrical base 190. The base 190 has a lip 192 that engages the countersunk bore 184 in the slide member 172. The base 190 has a first finger 194 and a second finger 196 depending therefrom. The fingers 194,196 are spaced to define an opening 197. The opening 197 receives the lead screw 154. Fingers 194 and 196 have first and second threaded portions 1989 respectively thereon that engage the threads 160 on the lead screw 154. Fingers 194 and 196 have first and second threaded portions 198 respectively thereon that engage the threads 160 on the lead screw 154. The threads 198 are positioned on generally opposed sides of the rotary nut 182. The base 190 further has an over-rotation surface 200 and a rotation surface 202.

Figure 24:
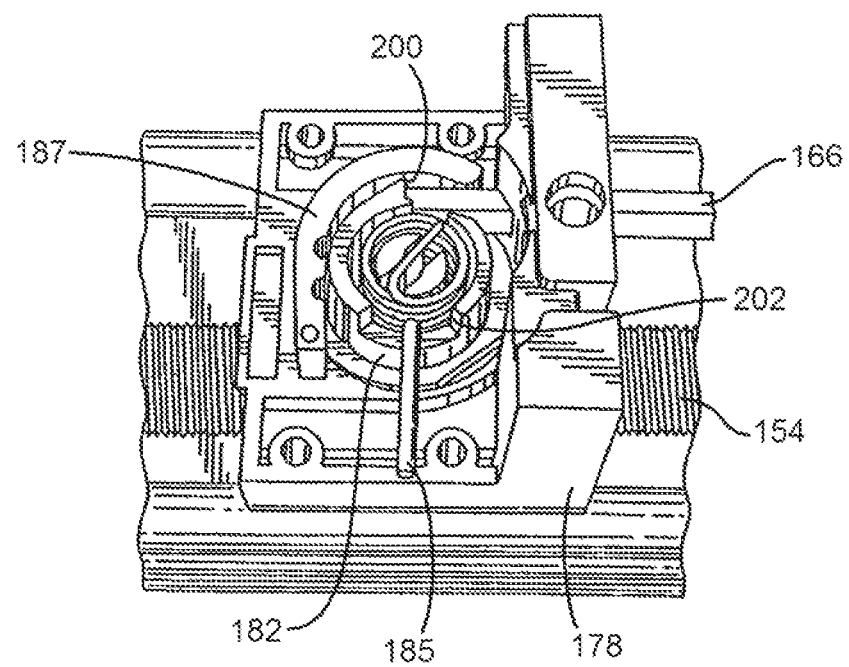
FIG. 24 is a partial perspective view of a slide assembly of the syringe drive mechanism having a rotary nut in a disengaged position.
Figure 25:
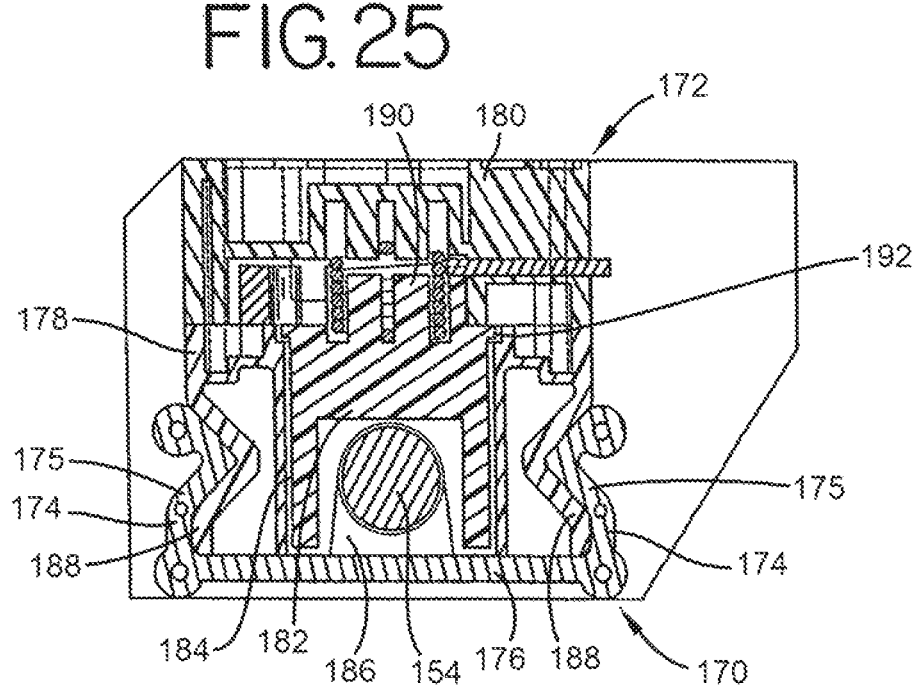
FIG. 25 is a cross-sectional view of the slide assembly of FIG. 24 in a disengaged position.
Figure 26:
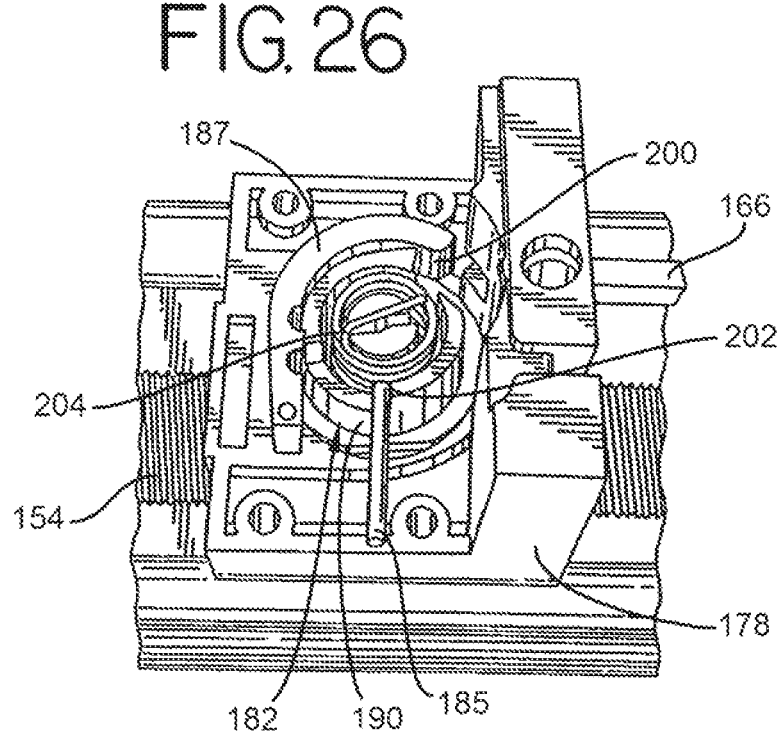
FIG. 26 is a partial perspective view of the slide assembly wherein the rotary nut is in an engaged position.
Figure 27:
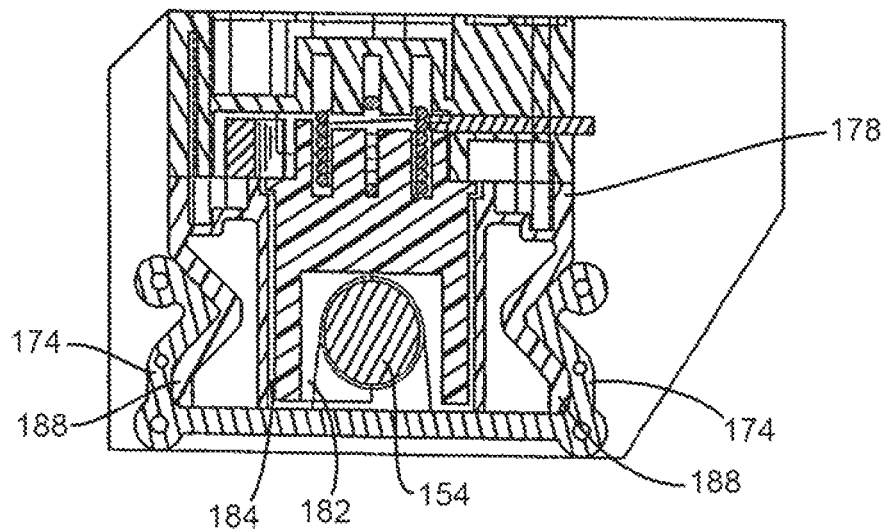
FIG. 27 is a cross-sectional view of the slide assembly of FIG. 26 in an engaged position.

As further shown in FIGS. 22-27, the rotary nut 182 is received in the cylindrical bore 184 in the slide member 172. The tube member 162 of the connecting linkage 156 is connected to the base 178 of the slide member 172. The slide member 172 is positioned for sliding movement on the rail member 170. The lead screw 154 is routed through the channel 186 in the slide member 172. FIGS. 26 and 27 show the rotary nut 182 in an engaged position with the lead screw 154. In FIG. 26, the cover 180 of the slide member 172 is removed for clarity. The rotary nut 182 is rotationally biased into engagement with the lead screw 154 by a spring 204. The threads 198 on each finger 192,194 of the rotary nut 182 engage generally opposed sides of the lead screw 154. The over-rotation surface 200 engages the pin 185 (carried by the cover 180) to prevent over-rotation of the nut 182 into the lead screw 154. This maximizes performance and minimizes wear of the threads 198 of the rotary nut 182. With the threads 198,160 engaged, when the motor 152 rotates the lead screw 154, the rotary nut 182 moves along the lead screw 154 which, in turn, linearly moves the slide member 172 and connecting linkage 156. This pushes the plunger 48 into the syringe barrel 46 to displace medicament from the syringe assembly 14. The lock arm 187 engages the base 190 of the rotary nut 182 to prevent the rotary nut 182 from disengaging under load such as from back pressure from the syringe assembly 14.

The rotary nut 182 can also be easily disengaged from the lead screw 154 which allows the slide member 172 to be positioned along the lead screw 154 such as when positioning the plunger engagement arm 164 against the syringe plunger 48. As shown in FIGS. 22, 24 and 25, the lever 168 is rotated on the plunger engagement arm 164. A camming action linearly moves the rod 166 within the tube member 162. The rod 166 engages the rotation surface 202 to rotate the rotary nut 182. The rotary nut 182 is rotated such that the threads 198 become disengaged from the threads 160 on the lead screw 154. This allows the slide member 172 to slide freely along the rail member 170 to position the plunger engagement arm 164.

The rotary nut 182 provides several advantages over previous nut/lead screw arrangements using single or multiple half-nuts that engage the lead screw. Half-nuts require a high rate spring to bias the nut into engagement with the lead screw and prevent disengagement. This requires transverse side loading of the lead screw that causes wear and mechanism inefficiency. Because the rotary nut 182 is a unitary piece, misalignment problems between two half-nuts is also eliminated. The rotary nut 182 utilizes a positive stop and lock. Therefore, side loads, moments, over engagement and disengagement during pumping are eliminated and wear is minimized.

The pump 10 is equipped with an occlusion sensor 22 to determine if an infusion line connected to the syringe barrel 46 is blocked. In one preferred embodiment of the invention, the occlusion sensor 22 is incorporated into the plunger engagement arm 164 of the drive mechanism 20. As shown schematically in FIG. 14, the occlusion sensor 22 generally includes a load cell 210 and a load beam 212. The load cell 210 is connected to a distal end of the plunger engagement arm 164. The load beam 212 is connected to generally a mid-portion of the arm 164 through a pivotal connection 214. The load beam 212 has a pusher block 216 that abuts against the end of the syringe plunger 48. The load cell 210 is positioned adjacent to and in contact with a distal end 218 of the load beam 212. Thus, one side of the load beam 212 contacts the load cell 210 and another side of the load beam 212 contacts the syringe plunger 48. A flipper 220 can extend from the arm 164 and be abutted against the plunger 48 to assure the plunger 48 always remains in contact with the pusher block 216.

In operation, the drive mechanism 20 drives the arm 164 as described above. This in turn drives the load beam 212 wherein the pusher block 216 pushes against the plunger 48. This forces and linearly moves the plunger 48 within the barrel 46. The load cell 210 measures a reactive force from the force pushing against the load beam 212. The circuitry associated with the load cell 210 converts the force to a usable signal. In a preferred embodiment, the usable signal is a voltage value. If too much force is required to move the plunger 48, it signifies that the infusion line is blocked. In such a case, the voltage detected is greater than a predetermined value, and the sensor 22 signals an occlusion in the infusion line. Thus, if the usable signal is out of a predetermined range, an occlusion is sensed. A user can then remedy the situation.

Figure 15:
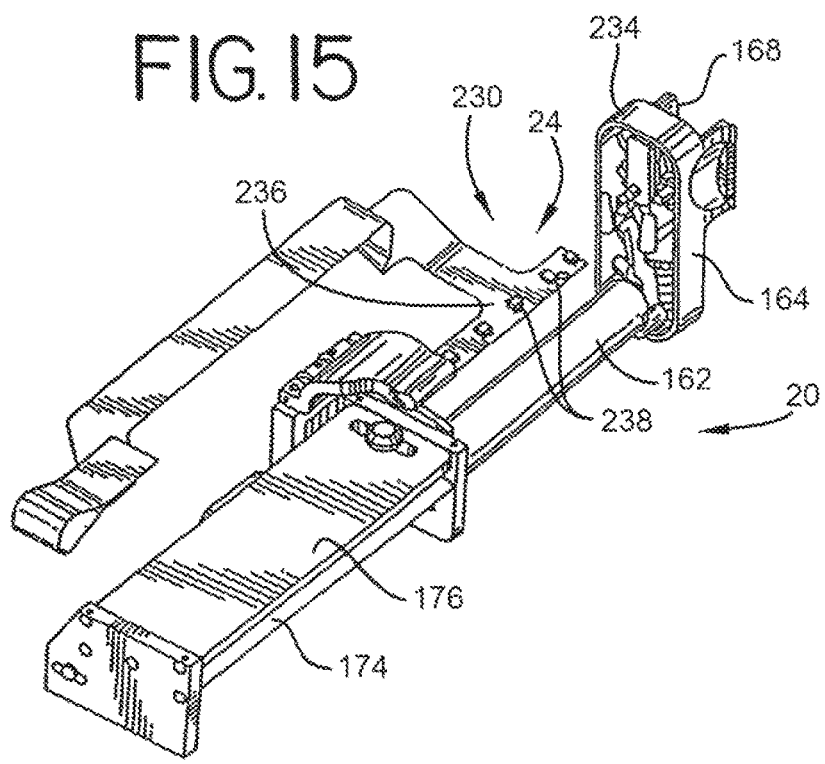
FIG. 15 is partial perspective view of the syringe drive mechanism and further showing a syringe plunger position indicator.
Figure 16:
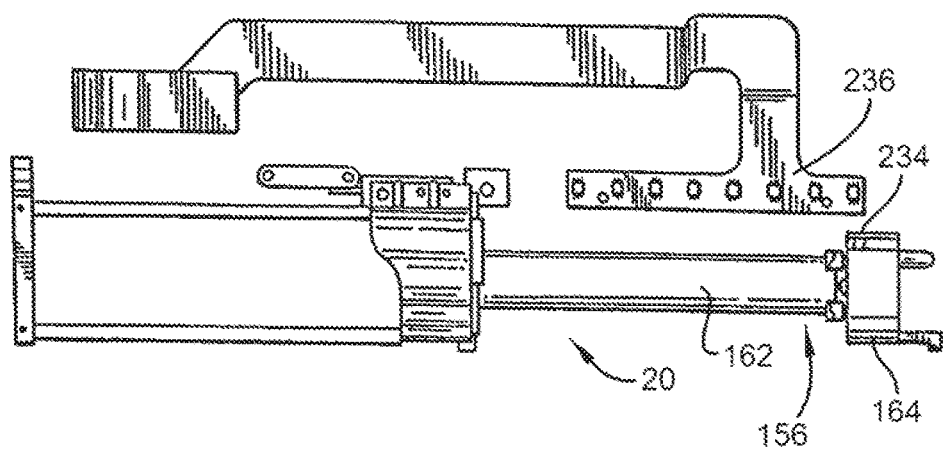
FIG. 16 is a partial plan view of the syringe drive mechanism and further showing the syringe plunger position indicator.

FIGS. 15-18 disclose various aspects of the syringe sensor system 24. The system 24 generally includes a syringe plunger position sensor 230 and a syringe barrel size sensor 232. FIGS. 15-17 disclose the syringe plunger position sensor 230. The sensor 230 is generally an eletromagnetic sensor that includes a magnet 234 and a plunger linear sensor array 236. The magnet 234 is mounted generally on the arm 164 of the connecting linkage 156 of the drive mechanism 20. The magnetic sensor in the form of a linear sensor array 236 has a plurality of sensors 238 in the form of magnets that are positioned directly adjacent to the linear path of the plunger movement. The magnet 234 has a magnetic field associated therewith. As shown in FIG. 16-17, the sensors 238 detect the orientation of the field lines in the magnetic field. The resulting signal is typically a sine wave. One sensor 238 has a specific length over which it can detect plunger movement. Then, the next sensor 238 will sense position. The sensors are initially calibrated wherein the pump software can determine the location of the plunger engagement arm 164 and, therefore, the plunger, based on the signal levels detected by each of the sensors 238. The magnet 234 is positioned substantially at a distal end of the plunger 48, or at the plunger head. The sensors 238 are directly adjacent the syringe plunger 48. With such a configuration, a direct measurement of the plunger position is possible rather than relying on indirect measurements. The sensors 238 are also configured to compensate for temperature changes as the pump 10 may be utilized in different environments.

FIG. 18 discloses the syringe barrel size sensor 232. Similar to the plunger position 30 sensor 230, the syringe barrel size sensor 232 is generally an electromagnetic sensor that includes a magnet 240 and a barrel linear sensor array 242. The magnet 240 is mounted on the syringe barrel clamp assembly. The linear sensor array 242 is mounted generally adjacent thereto and has a sensor 244. Because the movement of the syringe barrel clamp is less than the plunger movement, a single sensor 244 can be used. Similar to the syringe plunger position sensor, based on the signal levels sensed by the sensor 244, the sensor 232 can determine what size syringe is loaded into the pump 10.

In operation, the pump 10 is mounted on a support structure such as a pole in either a horizontal or vertical configuration as shown in FIGS. 3a and 3b. The access door 36 is opened and a syringe assembly 14 is loaded into the pump 10. As shown in FIGS. 1, 2 and 19, the syringe assembly 14 can be conveniently loaded into the pump 10 with a single hand. Prior art pumps require both hands of a user to load the syringe. As shown in FIG. 2, the curved lip 50 allows the syringe 14 to slide easily into the syringe compartment 34. As shown in FIG. 19, the rollers 56,58 associated with the syringe barrel clamp 52 allows the clamp 52 to slide upwards along the housing 12 in accepting the syringe 14 as in a snap-fit arrangement. When the syringe 14 is further inserted, the clamp 52 is biased back onto the syringe barrel 46. The infusion line is attached to the syringe and connected intravenously to a patient. The access door 36 is locked. The operating parameters of the pump 10 are loaded into the pump software through the user interface 16. The infusion therapy can then be started.

The pump 10 can be equipped with several different features to enhance its operability. For example, the pump can accommodate patient-controlled analgesia (PCA). To that end and as shown in FIG. 2, the pump 10 can have a PCA button 299 wherein a user can further control the infusion therapy wherein the user can push the button to deliver additional doses of medication. The PCA button typically has a cord that can be plugged into the pump 10 as is generally known. The button 299 can be specially designed to be activated by a thumb of a patient. As further shown in FIG. 2, the button 299 can also be equipped with a fingerprint reader 301 to assure only the patient can activate the PCA button 299. The fingerprint reader 301 is operably connected to the user interface 16. The patient's fingerprint or thumbprint can be pre-loaded into the pump software of the user interface 16. When the PCA button 299 is pushed, and the reader 301 reads the thumbprint, the software verifies the button 299 was pushed by the patient by comparing the print that was read with the stored thumbprint. The PCA button 299 can have peripheral structure to protect inadvertent actuation. The PCA button 299 can also be lighted so as so glow in the dark to aid patients in locating the button.

FIGS. 31-33 disclose additional features associated with the PCA button 299. FIGS. 31 and 32 show wiring diagrams 300 and 301 for the PCA button. Wiring diagrams 300 and 301 include a first circuit 302, a second circuit 304, a third circuit 306, a common ground 308, and a 4-pole push button 310 carried by the PCA button 299. FIG. 31 shows a wiring diagram 300 having the push button 310 in an at rest position. FIG. 32 shows wiring diagram 301 having the push button 310 in an actuated position. As shown in FIGS. 31 and 32, circuits 302, 304, and 306 share a common ground 308. Though a common ground 308 is the simplest way to wire circuits 302, 304, and 306, it is not required for the invention that the circuits 302, 304, and 306 share a common ground 308, as long as the circuits are able to provide signals to a microprocessor associated with the pump user interface 16. Circuits 302, 304, and 306 are designed to provide a status change in signal to the microprocessor. The status change may occur due to the installation of the PCA button 299 and associated wiring 312. The status change may also occur due to a circuit being connected to ground through push button 310 versus when the circuits are open. Wiring 312 may be enclosed in a cable.

Circuits 302, 304, and 306 are maintained at an energized state when not connected to ground 308 through button 310. Conversely, circuits 302, 304, and 306 are at a ground state when connected to ground 308 through button 310. For example, circuits 302, 304, and 306 may maintain a small positive voltage when not connected to ground 308 through button 310. The small positive voltage may be coordinated with desired input signals for the microprocessor while considering the safety requirements of the medical environment.

As circuits 302, 304, and 306 are maintained at an energized state, also known as a "HIGH" state, when not connected to ground, the circuits will all be in a HIGH state when button 310 is not installed. Installation may involve connecting the button 310 to the wiring 312. Installation may also involve connecting the PCA button 299, and therefore, pushbutton 310 and wiring 312 to infusion pump 10.

Wiring diagram 300 shows push button 310 in an at rest installed position. When button 310 is in the at rest installed position, first circuit 302 is connected to ground directly through wiring 312 and through contacts 310b and 310a and is therefore in the ground state, or "LOW" state. When button 310 is in the actuated position as shown in wiring diagram 301, first circuit 302 is still connected to ground directly through wiring 312 and through contacts 310c and 310d and is therefore in the LOW state as long as button 310 is installed.

When button 310 is in the at rest installed position, second circuit 304 is connected to ground 308 through contact 310a and is therefore in the LOW state. When button 310 is in the actuated position as shown in wiring diagram 301, second circuit 304 is not connected to ground 308 and is therefore in the HIGH state.

When button 310 is in the at rest installed position, third circuit 306 is not connected to ground 308 and is therefore in the HIGH state. When button 310 is in the actuated position as shown in wiring diagram 301, third circuit 306 is connected to ground through contacts 310c and 310d and is therefore in the LOW state.

FIG. 33 shows a table 400 summarizing information provided by the status signals of the three PCA circuits 302, 304, and 306 of FIGS. 31 and 32. Table 400 shows that the PCA button is not installed if circuits 302, 304, and 306 are all providing a HIGH status signal. If first circuit 302 and second circuit 304 are providing a LOW status signal, while circuit three is providing a HIGH status signal, the button 310 is installed and is in the rest position. If first circuit 302 and third circuit 306 are providing a LOW status signal, while second circuit 304 is providing a HIGH status signal, the button 310 is installed and is actuated. Various other combinations of status signals indicate that a fault exists. Potential faults include, but are not limited to, cable failures, switch malfunctions, and electronic circuit malfunctions. Thus, if one of the wires associated with the PCA button 299 becomes frayed and eventually breaks, a specific reading can be sensed by the user interface to indicate the PCA button 299 requires replacement.

The pump 10 can also be designed with enhanced communication capabilities. For example, the pump 10 can communicate wirelessly with other devices such as a pharmacy computer or personal digital assistants (PDA) carried by hospital personnel. The pump 10 can also be monitored remotely such as from a nurse's station. The pump 10 can be equipped with various types of readers to receive patient information such as from swipe cards or bar-coded identification bracelets. The pump 10 may also utilize RFID readers and tags as discussed above.

In one preferred embodiment of the invention, the pump 10 can communicate with a PDA 500 as shown in FIG. 2. The pump 10 has the infrared data port 76 that is operably coupled with the user interface 16 of the pump 10. The user interface 16 has memory that stores information regarding pump history such as medications delivered, dosage, time, date etc. The information stored by the user interface 16 can be electronically transferred to the PDA 500 carried, for example, by medical personnel. For example, the history button 74 can be depressed on the pump control panel indicating a desire to download pump history. The pump 10 will prompt the user for a password on the video display 60. The password may be necessary for certain regulatory requirements. The pump 10 will then prompt the user for a patient identification number so the proper pump history can be identified. The pump 10 then prompts the user to position the PDA 500 up to the data port 76. Once positioned properly, the pump 10 downloads the proper pump history to the PDA 500. The user can then view the data on the PDA 500, print the pump history or sync the data to another computer as desired. The data can be formatted to be in paginated form.

The pump 10 may also communicate directly to a printer. In one embodiment, a hand-held printer having an appropriate data port, can be held up to the data port 76 of the pump 10. Via infrared communication, data can be transferred from the pump 10 and printed by the hand-held computer.

As discussed, the pump 10 provides several advantages. The pump 10 can be powered by either a rechargeable battery unit or a disposable battery unit as is desired by the user. Separate pumps are not required. Because the pump 10 can be powered by battery units, the pump 10 can be used in locations where there are limited electrical outlets. Furthermore, because the transformer for recharging the batteries is contained within the rechargeable battery unit rather than the pump, the rechargeable battery unit can be recharged simply by plugging the unit into a wall outlet. The pump is not required. Accordingly, the pump 10 can be equipped with a second unit and remain in use while the first unit is being recharged. Also, the transformer is better stored within the battery unit housing rather than being located at the end of the power cord. The syringe loaded is improved as a syringe assembly can be easily loaded with a single hand. The syringe sensors are improved and are more reliable. The sensors provide a direct measurement of, for example, plunger position rather than an indirect measurement. The magnet and sensors are positioned directly at the syringe plunger providing a direct measurement of plunger position. The sensor system has fewer parts in general and does not utilize additional moving parts that are subject to wear. This improves reliability. The rotary nut associated with the drive mechanism provides a more smooth and reliable mechanism.

While the specific embodiments have been illustrated and described, numerous modifications can be made to the present invention, as described, by those of ordinary skill in the art without significantly departing from the spirit of the invention. The breadth of protection afforded this invention should be considered to be limited only by the scope of the accompanying claims.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. An infusion pump operable with a syringe having a syringe barrel and a syringe plunger moveable within the syringe barrel, the infusion pump comprising:
   a housing structured to receive the syringe, the housing including a syringe clamp for contacting the syringe barrel;
   a drive mechanism supported by the housing, the drive mechanism structured and arranged to contact and end of the syringe plunger so as to be able to move the syringe plunger within the syringe barrel;
   a syringe barrel size sensor including
      a magnet moveable with the syringe clamp when clamping the syringe barrel, and
      a sensing member supported by the housing and configured to generate an output indicative of a magnetic field associated with the magnet; and
   software installed on the pump and programmed to use the output to determine a size of the syringe barrel received by the compartment.

2. The infusion pump of claim 1, wherein the magnet is positioned on the syringe clamp.

3. The infusion pump of claim 1, wherein the sensing member includes a plurality of electromagnetic sensors.

4. The infusion pump of claim 1, wherein the sensing member includes a linear sensor array.

5. The infusion pump of claim 1, wherein the sensing member includes a single electromagnetic sensor.

6. The infusion pump of claim 1, wherein the sensing member is mounted adjacent to the magnet.

7. The infusion pump of claim 1, wherein the housing includes a compartment structured to receive the syringe and defining a wall, and wherein the syringe clamp is moveable towards and away from the wall, the syringe clamp contacting the syringe barrel when the syringe clamp is moved towards the wall.

8. An infusion pump operable with a syringe having a syringe barrel and a syringe plunger moveable within the syringe barrel, the infusion pump comprising:
   a housing including a syringe clamp resiliently biased to hold the syringe barrel;
   a drive mechanism supported by the housing, the drive mechanism structured and arranged to contact and end of the syringe plunger so as to be able to move the syringe plunger within the syringe barrel;
   a syringe barrel size sensor including
      a magnet operably coupled to the syringe clamp, and
      a sensing member provided adjacent to the magnet and configured to generate an output indicative of a magnetic field associated with the magnet; and
   software installed on the pump and programmed to use the output to determine a size of the syringe barrel received by the compartment.

9. The infusion pump of claim 8, wherein the magnet is positioned on the syringe clamp.

10. The infusion pump of claim 8, wherein the sensing member includes a plurality of electromagnetic sensors, a linear sensor array, or a single electromagnetic sensor.

11. The infusion pump of claim 8, wherein the syringe clamp is slideable within the compartment.

12. The infusion pump of claim 8, wherein the housing includes a compartment structured to receive the syringe, and wherein the syringe clamp is moveable within the compartment and resiliently biased to hold the syringe barrel within the compartment.

13. The infusion pump of claim 12, wherein the compartment includes a wall, and wherein the syringe clamp is moveable relative to the wall to hold the syringe barrel in a resiliently biased manner.

14. An infusion pump method comprising:
   sensing a magnetic field associated with a first magnet coupled to a syringe clamp to determine a size of a syringe barrel received in a housing of an infusion pump; and
   sensing a magnetic field associated with a second magnet to determine a linear position of a syringe plunger moveable inside the syringe barrel.

15. The infusion pump method of claim 14, which includes linearly sensing the magnetic field associated with the first magnet to determine the size of the syringe barrel.

16. The infusion pump method of claim 14, which includes linearly sensing the magnetic field associated with the second magnet to determine the linear position of the syringe plunger moveable inside the syringe barrel.

17. The infusion pump method of claim 14, which includes sensing an orientation of magnetic field lines associated with (i) the first magnet and (ii) the second magnet to determine (a) the size of the syringe barrel and (b) the linear position of the syringe plunger moveable within the syringe barrel, respectively.

18. The infusion pump method of claim 14, which includes positioning the second magnet on a drive mechanism supported by the housing, the drive mechanism structured and arranged to contact the syringe plunger and move the syringe plunger within the syringe barrel.

19. The infusion pump method of claim 14, wherein sensing the magnetic field associated with the first magnet includes using a sensing member supported by a housing of the infusion pump, the sensing member configured to generate an output indicative of a magnetic field associated with the first magnet.

20. The infusion pump method of claim 19, wherein determining the size of the syringe barrel received in the housing of the infusion pump includes providing software programmed to analyze the output indicative of the magnetic field associated with the first magnet.

21. The infusion pump method of claim 14, wherein sensing the magnetic field associated with the second magnet includes using a magnetic sensor array supported by a housing of the infusion pump positioned adjacent to the magnet, the magnetic sensor array configured to generate an output indicative of a magnetic field associated with the second magnet.

22. The infusion pump method of claim 21, wherein sensing the magnetic field associated with the second magnet to determine the linear position of the syringe plunger moveable inside the syringe barrel includes providing software programmed to analyze the output indicative of the magnetic field associated with the second magnet.

* * * * *